United States Patent
Padmanabhan et al.

(10) Patent No.: US 11,157,484 B2
(45) Date of Patent: Oct. 26, 2021

(54) ADVANCED SMART CONTRACT WITH DECENTRALIZED LEDGER IN A MULTI-TENANT ENVIRONMENT

(71) Applicant: salesforce.com, inc., San Francisco, CA (US)

(72) Inventors: Prithvi Krishnan Padmanabhan, San Ramon, CA (US); Sri Naga Deepthi Velisetti, Dublin, CA (US); Philip Norman Calvin, San Francisco, CA (US); Brent Fosdick, Fort Collins, CO (US)

(73) Assignee: salesforce.com, inc., San Francisco, CA (US)

( * ) Notice: Subject to any disclaimer, the term of this patent is extended or adjusted under 35 U.S.C. 154(b) by 201 days.

(21) Appl. No.: 16/228,528

(22) Filed: Dec. 20, 2018

(65) Prior Publication Data
US 2020/0089671 A1 Mar. 19, 2020

Related U.S. Application Data

(60) Provisional application No. 62/733,531, filed on Sep. 19, 2018.

(51) Int. Cl.
*G06F 16/23* (2019.01)
*H04L 9/06* (2006.01)
(Continued)

(52) U.S. Cl.
CPC .......... *G06F 16/2379* (2019.01); *G06F 16/27* (2019.01); *H04L 9/0637* (2013.01); *G16H 10/60* (2018.01); *H04L 2209/38* (2013.01)

(58) Field of Classification Search
CPC ... G06F 16/2379; G06F 16/27; H04L 9/0637; H04L 2209/38; G16H 10/60
(Continued)

(56) References Cited

U.S. PATENT DOCUMENTS

| 7,730,478 | B2 | 6/2010 | Weissman |
| 8,326,876 | B1 | 12/2012 | Venkataraman et al. |

(Continued)

FOREIGN PATENT DOCUMENTS

| WO | 2016161073 A1 | 10/2016 |
| WO | 2018007828 A2 | 1/2018 |

OTHER PUBLICATIONS

International Search Report and Written Opinion, Intl. App. No. PCT/US2019/051781, dated Dec. 10, 2019, 13 pages.

(Continued)

*Primary Examiner* — Hares Jami
(74) *Attorney, Agent, or Firm* — Nicholson, De Vos, Webster & Elliott, LLP

(57) ABSTRACT

A method for a multi-tenant server to manage data in a peer-to-peer blockchain network is described. The method includes monitoring one or more fields of a first physical object of a first tenant in the peer-to-peer blockchain network to determine when one or more conditions of a smart contract have been fulfilled; determining that one or more conditions of the smart contract have been met by the first physical object of the first tenant; and performing one or more operations of the smart contract, which are associated with the one or more conditions, in response to determining that the one or more conditions of the smart contract have been met by the first physical object of the first tenant, wherein the one or more operations are performed in relation to a second physical object of a second tenant in the peer-to-peer blockchain network.

17 Claims, 11 Drawing Sheets

(51) Int. Cl.
*G06F 16/27* (2019.01)
*G16H 10/60* (2018.01)

(58) Field of Classification Search
USPC .......................................................... 707/703
See application file for complete search history.

(56) References Cited

U.S. PATENT DOCUMENTS

| | | | |
|---|---|---|---|
| 8,886,671 | B1 | 11/2014 | Ro et al. |
| 9,075,889 | B2 | 7/2015 | Calvin et al. |
| 9,276,995 | B2 | 3/2016 | Calvin et al. |
| 9,317,843 | B2 | 4/2016 | Bradley et al. |
| 9,448,773 | B2 | 9/2016 | Calvin et al. |
| D768,690 | S | 10/2016 | Conn |
| 9,525,720 | B2 | 12/2016 | Calvin et al. |
| 9,572,614 | B2 | 2/2017 | Calvin et al. |
| 9,635,090 | B2 | 4/2017 | Calvin et al. |
| D800,148 | S | 10/2017 | Conn |
| 9,811,506 | B2 | 11/2017 | Calvin |
| 9,992,022 | B1 | 6/2018 | Chapman et al. |
| 10,027,735 | B2 | 7/2018 | Calvin et al. |
| 10,117,697 | B2 | 11/2018 | Calvin et al. |
| 10,212,209 | B2 | 2/2019 | Calvin et al. |
| 10,489,786 | B2 | 11/2019 | Yu et al. |
| 2002/0194501 | A1 | 12/2002 | Wenocur et al. |
| 2003/0149934 | A1 | 8/2003 | Worden |
| 2008/0034228 | A1 | 2/2008 | Shear et al. |
| 2010/0005443 | A1 | 1/2010 | Kwok et al. |
| 2011/0276490 | A1 | 11/2011 | Wang et al. |
| 2013/0290406 | A1 | 10/2013 | Calvin et al. |
| 2014/0122649 | A1 | 5/2014 | Calvin et al. |
| 2014/0122993 | A1 | 5/2014 | Calvin et al. |
| 2014/0304692 | A1 | 10/2014 | Calvin et al. |
| 2015/0127781 | A1 | 5/2015 | Calvin et al. |
| 2015/0348017 | A1 | 12/2015 | Allmen |
| 2015/0379510 | A1 | 12/2015 | Smith |
| 2016/0012465 | A1 | 1/2016 | Sharp |
| 2016/0021166 | A1 | 1/2016 | Calvin et al. |
| 2016/0048481 | A1 | 2/2016 | Calvin |
| 2016/0088058 | A1 | 3/2016 | Calvin et al. |
| 2016/0098723 | A1 | 4/2016 | Feeney |
| 2016/0162873 | A1 | 6/2016 | Zhou et al. |
| 2016/0164947 | A1 | 6/2016 | Calvin et al. |
| 2017/0048301 | A1 | 2/2017 | Calvin et al. |
| 2017/0140408 | A1* | 5/2017 | Wuehler ............. G06Q 30/0207 |
| 2017/0178127 | A1* | 6/2017 | Kravitz ................ G06Q 20/401 |
| 2017/0252085 | A1 | 9/2017 | Calvin et al. |
| 2017/0337534 | A1 | 11/2017 | Goeringer et al. |
| 2017/0344618 | A1 | 11/2017 | Horowitz et al. |
| 2018/0005186 | A1 | 1/2018 | Hunn |
| 2018/0006831 | A1 | 1/2018 | Toll et al. |
| 2018/0018723 | A1 | 1/2018 | Nagla et al. |
| 2018/0173719 | A1* | 6/2018 | Bastide ................... G06F 16/13 |
| 2018/0219676 | A1 | 8/2018 | Mattingly et al. |
| 2018/0248880 | A1 | 8/2018 | Sardesai et al. |
| 2018/0285322 | A1 | 10/2018 | Calvin |
| 2019/0005268 | A1 | 1/2019 | Gupta |
| 2019/0058709 | A1 | 2/2019 | Kempf et al. |
| 2019/0087446 | A1* | 3/2019 | Sharma ................ G06Q 20/382 |
| 2019/0087449 | A1* | 3/2019 | Rybacki ................ G06F 16/284 |
| 2019/0179951 | A1 | 6/2019 | Brunet et al. |
| 2019/0236559 | A1 | 8/2019 | Padmanabhan |
| 2019/0236562 | A1 | 8/2019 | Padmanabhan |
| 2019/0236598 | A1 | 8/2019 | Padmanabhan |
| 2019/0236606 | A1 | 8/2019 | Padmanabhan et al. |
| 2019/0238316 | A1 | 8/2019 | Padmanabhan |
| 2019/0238525 | A1 | 8/2019 | Padmanabhan et al. |
| 2019/0303121 | A1 | 10/2019 | Padmanabhan |
| 2019/0303445 | A1 | 10/2019 | Padmanabhan |
| 2019/0377806 | A1 | 12/2019 | Padmanabhan et al. |
| 2019/0379721 | A1 | 12/2019 | Calvin et al. |
| 2020/0042939 | A1 | 2/2020 | Padmanabhan |
| 2020/0074457 | A1 | 3/2020 | Coleman et al. |
| 2020/0084027 | A1 | 3/2020 | Duchon et al. |
| 2020/0185070 | A1* | 6/2020 | Dahmani ............ G06F 21/6245 |

OTHER PUBLICATIONS

International Search Report and Written Opinion, Intl. App. No. PCT/US2019/051782, dated Jan. 10, 2020, 12 pages.
International Search Report and Written Opinion, Intl. App. No. PCT/US2019/051783, dated Dec. 11, 2019, 11 pages.
Nakamoto, Satoshi, "Bitcoin: A Peer-to-Peer Electronic Cash System", Satoshi Nakamoto Institute, Oct. 31, 2008, 9 pages.
Xia et al., "MeDShare: Trust-Less Medical Data Sharing Among Cloud Service Providers via Blockchain" IEEE Access, vol. 5, 2017, pp. 14757-14767.
Yu et al., "Virtualization for Distributed Ledger Technology (vDLT)", IEEE Access, vol. 6, 2018, pp. 25019-25028.
International Search Report and Written Opinion for Application No. PCT/US2019/036103, dated Aug. 1, 2019, 12 pages.
Non-Final Office Action, U.S. Appl. No. 16/228,555, dated Jan. 13, 2021, 13 pages.
Non Final Office Action, U.S. Appl. No. 16/228,501, dated Oct. 28, 2020, 10 pages.
Non-Final Office Action, U.S. Appl. No. 16/228,569, dated May 13, 2021, 15 pages.
Non-Final Rejection, U.S. Appl. No. 16/136,077, dated Jun. 9, 2021, 11 pages.
Notice of Allowance, U.S. Appl. No. 16/228,501, dated Apr. 13, 2021, 8 pages.
Notice of Allowance, U.S. Appl. No. 16/228,555, dated Apr. 30, 2021, 11 pages.

\* cited by examiner

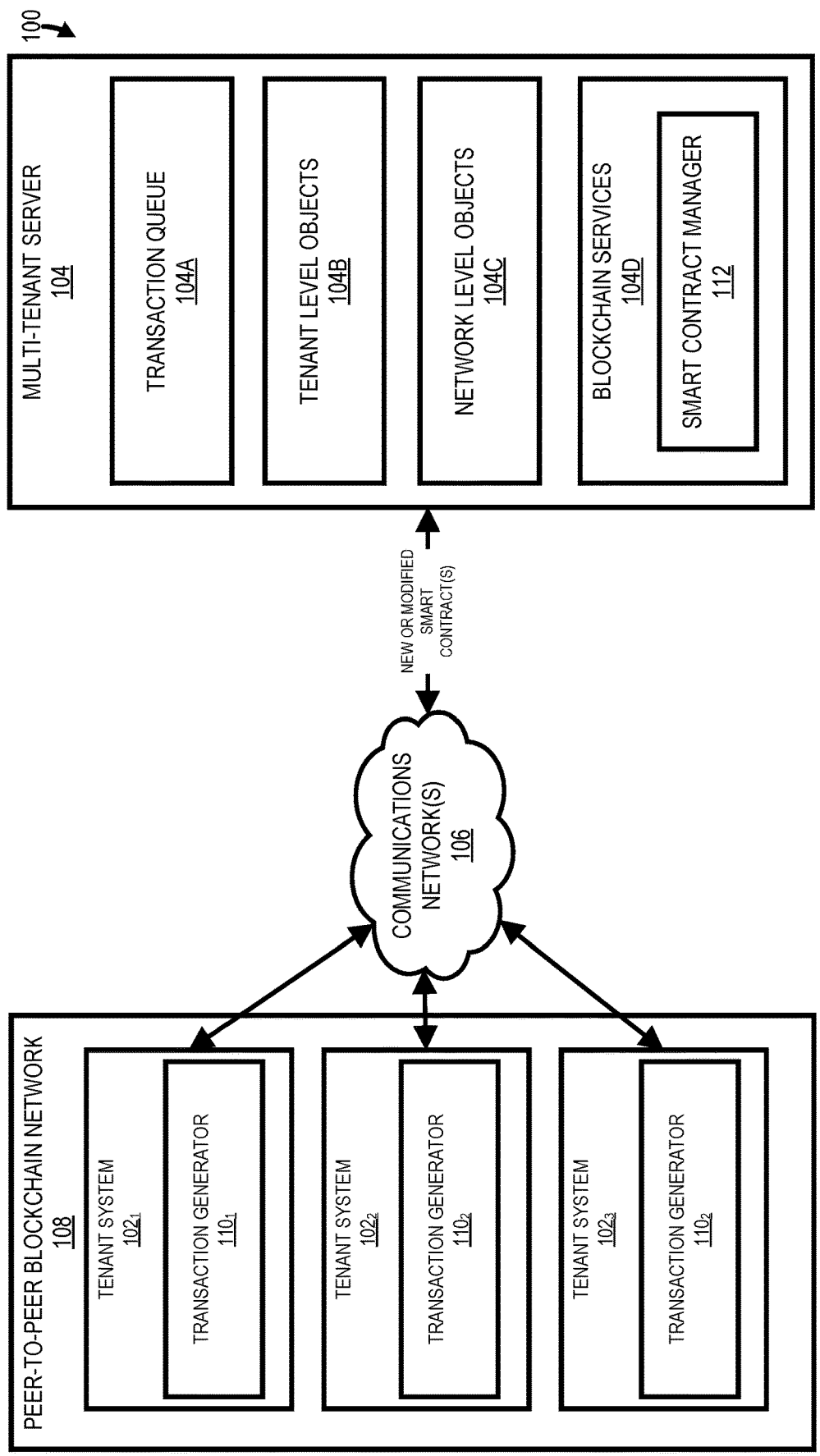

| TRANSACTION OBJECT 702 |||||
|---|---|---|---|---|
| EXCHANGE FIELD $504_1$ | EXCHANGE FIELD $504_2$ | ... || EXCHANGE FIELD $504_P$ |
| FIELD VALUE $606_{1,H}$ | FIELD VALUE $606_{1,1}$ | ... || FIELD VALUE $606_{1,2}$ |

ADVANCED SMART CONTRACT WITH DECENTRALIZED LEDGER IN A MULTI-TENANT ENVIRONMENT

CROSS-REFERENCE TO RELATED APPLICATIONS

This application claims the benefit of U.S. Provisional Application No. 62/733,531, filed Sep. 19, 2018, which is hereby incorporated by reference.

TECHNICAL FIELD

One or more implementations relate to the field of data management; and more specifically, to managing smart contracts in a multi-tenant blockchain network.

BACKGROUND

A blockchain is a continuously expanding list of records/blocks that are linked and secured using cryptography. In particular, every block in a blockchain may include a cryptographic hash of the immediately preceding block, a timestamp for the current block, and transaction data (e.g., the addition/modification of information associated with a peer in a blockchain network). Further, the blockchain may be shared and managed through a peer-to-peer network via a system of verifying/validating new blocks to be added to the chain such that a block in a blockchain cannot be altered without alteration of all subsequent blocks, which requires network consensus. This architecture allows for security of information stored within blocks through the use of cryptography; sharing/distribution of information through the use of peer-to-peer networks; trust through the use of consensus of block addition; and immutability of information stored within blocks through the use of cryptography, chaining/linking of blocks, and peer distribution (e.g., each peer in the blockchain network may maintain a ledger of all verified/validated transactions in the network).

Some blockchain networks may operate with smart contracts. Smart contracts are cryptographically verifiable contracts that are enforced without a trusted third party. In particular, a smart contract includes code that describes a set of conditions and a set of operations that are selectively performed in response to meeting one or more condition in the set of conditions. For example, a smart contract may stipulate that when a first party accomplishes a task, digital currency from a second party will be transferred into an account of the first party. These smart contracts are stored in a blockchain network and, based on their inclusion in a blockchain network, are immutable.

In contrast to a blockchain architecture, a multi-tenant cloud architecture relies on centralization of information in a common database or other data structure. Although cloud-based architectures provide many benefits in comparison to blockchain architectures, including the ability to remove many management functions from tenants and instead focus these functions on a centralized system, these architectures do not provide the same level of security, trust, and immutability of information during inter-tenant communications of data.

BRIEF DESCRIPTION OF THE DRAWINGS

The following figures use like reference numbers to refer to like elements. Although the following figures depict various exemplary implementations, alternative implementations are within the spirit and scope of the appended claims. In the drawings:

FIG. 1 shows a block diagram illustrating a computing environment, including a multi-tenant server, according to one example implementation.

FIG. 7 shows an example of a transaction object, according to one example implementation.

DETAILED DESCRIPTION

Figure 2A:
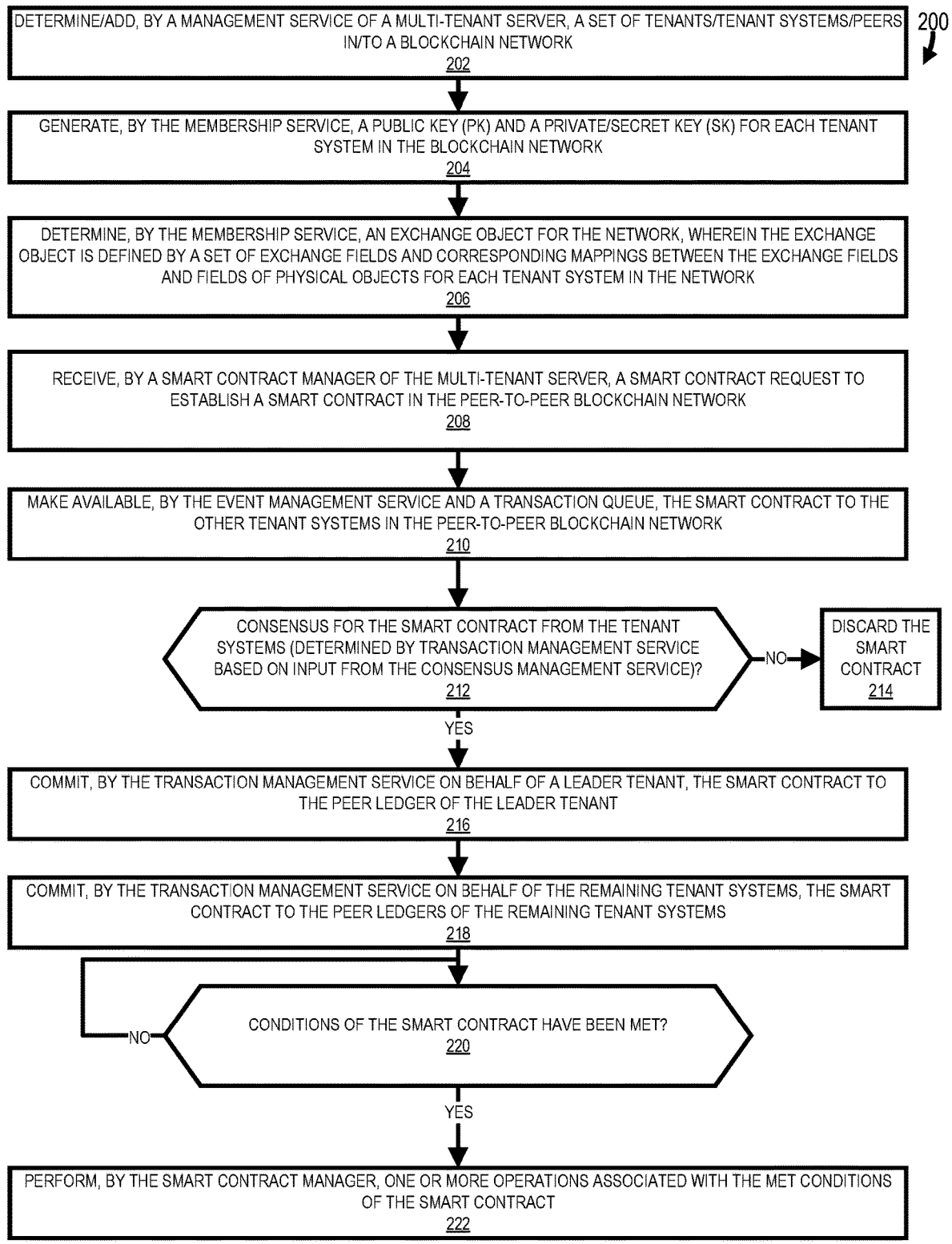
FIGS. 2A and 2B show a method for the multi-tenant server to manage data in a peer-to-peer blockchain network, including management of smart contracts, according to one example implementation.

FIG. 1 is a block diagram illustrating a computing environment 100, according to one example implementation. The computing environment 100 includes tenant systems $102_1$-$102_3$, a multi-tenant server 104, and a set of communications networks 106. In this example computing environment 100, the tenant systems $102_1$-$102_3$ may be part of a peer-to-peer blockchain network 108 and the multi-tenant server 104 provides a cloud environment to manage data and various transactions of the tenant systems $102_1$-$102_3$ in the peer-to-peer blockchain network 108 via a transaction queue 104A, tenant level objects 104B, network level objects 104C, and blockchain services 104D. In particular, the multi-tenant server 104 provides management of smart contracts through the smart contract manager 112, which is part of the blockchain services 104D.

As will be described herein, the tenant systems $102_1$-$102_3$ are part of a multi-tenant environment/system that is managed by the multi-tenant server 104. For example, the multi-tenant server 104 may manage a multi-tenant database management system (DBMS) in which the users/tenants associated with the tenant systems $102_1$-$102_3$ are able to store and/or retrieve data. A multi-tenant DBMS refers to those systems in which various elements of hardware and software of the DBMS may be shared by one or more tenants (e.g., the tenant systems $102_1$-$102_3$). For example, a given server (e.g., the multi-tenant server 104) may simultaneously process requests for a great number of tenants (e.g., represented by the tenant systems $102_1$-$102_3$), and a given database table may store records for a potentially much greater number of tenants. In addition to managing a multi-tenant environment/system for the tenant systems $102_1$-

$102_3$, as noted above, the multi-tenant server 104 may also manage the peer-to-peer blockchain network 108 on behalf of the tenant systems $102_1$-$102_3$. In some embodiments, the peer-to-peer blockchain network 108 may be viewed as a distributed network that is controlled by the multi-tenant server 104 with inputs/requests from the tenant systems $102_1$-$102_3$.

Although shown with three tenants/peers (e.g., the tenant systems $102_1$-$102_3$), in other implementations, the peer-to-peer blockchain network 108 may include more or fewer tenants/peers. For example, the peer-to-peer blockchain network 108 may include two, four, five, or more tenants/peers with corresponding tenant systems 102. Accordingly, the use of three tenants/peers is for illustrative purposes.

In some implementations, a transaction generator 110 of a tenant system 102 may generate a request to (1) add a new record to a physical object associated with the tenant system 102 or (2) modify an existing record of the physical object associated with the tenant system 102. The physical object may include a set of fields for each record and is stored in a portion/partition of the tenant level objects 104B of the multi-tenant server 104 associated with the corresponding tenant system 102 such that the physical object is only accessible to the tenant system 102 (e.g., the tenant systems $102_2$ and $102_3$ are not permitted to read or write to the physical object of the tenant system $102_1$). The request may cause the addition of a record in a shadow object in the portion/partition of the tenant level objects 104B associated with the tenant system 102. The shadow object represents uncommitted data to the physical object (i.e., data for which a consensus amongst the peers in the peer-to-peer blockchain network 108 has not yet been achieved). The shadow object may be used by the transaction queue 104A for generating a transaction object, which will be distributed/made available to the other tenant systems 102 for receiving consensus for the proposed addition/modification to the physical object of the tenant system 102.

In one implementation, the set of fields of the transaction object is a subset of the fields of the physical object and the set of fields of the transaction object are defined by an exchange object, which is included in the network level objects 104C. In this implementation, the exchange object may include a set of exchange fields, which will be included in the transaction object, and each exchange field of the exchange object is mapped to a field in the physical objects of the tenant systems $102_1$-$102_3$. For example, a physical object of the tenant system $102_1$ may include fields A-D, a physical object of the tenant system $102_2$ may include fields E-H, and a physical object of the tenant system $102_3$ may include fields I-K. In this example, a first exchange field of the exchange object of the peer-to-peer blockchain network 108 may be mapped to the field B of the tenant system $102_1$, the field F of the tenant system $102_2$, and the field I of the tenant system $102_3$. Similarly, a second exchange field of the exchange object of the peer-to-peer blockchain network 108 may be mapped to the field C of the tenant system $102_1$, the field E of the tenant system $102_2$, and the field J of the tenant system $102_3$. Accordingly, when a proposal for adding/modifying a record for the physical object of the tenant system $102_1$ is received, the corresponding transaction object includes the first exchange field with a value from field B of the proposed physical/shadow object and the second exchange field with a value from field C of the proposed physical/shadow object. The exchange object provides a uniform transaction object via mapping metadata for verification/validation purposes in the peer-to-peer blockchain network 108 while allowing the tenant system $102_1$ to only reveal particular portions of information to other tenants/peers in the peer-to-peer blockchain network 108 (e.g., sensitive information/fields in physical objects may not be included in transaction objects which are distributed amongst tenant systems $102_1$-$102_3$ in the peer-to-peer blockchain network 108 and later included in distributed ledgers).

As described herein, the multi-tenant server 104 may perform many of the functions of the peer-to-peer blockchain network 108 on behalf of the tenant systems $102_1$-$102_3$. In particular, the multi-tenant server 104 may include a virtual space/organization for each of the tenant systems $102_1$-$102_3$. Each virtual space/organization may include data and applications/services for corresponding tenant systems $102_1$-$102_3$ and is logically separate from all other virtual spaces/organizations of other tenant systems $102_1$-$102_3$. For example, each virtual space/organization may include tenant level objects 104B corresponding to respective tenants/tenant systems $102_1$-$102_3$ and separate instantiations of or access to blockchain services 104D. In this configuration/architecture, the virtual space/organization for each tenant system $102_1$-$102_3$ may perform one or more blockchain functions/operations on behalf of the corresponding tenant system $102_1$-$102_3$. For example, in response to receipt of a request from the tenant system $102_1$ to add/insert a new record to or modify/update an existing record of a physical object of the tenant system $102_1$, the multi-tenant server 104 may generate a shadow object record in the virtual space/organization of the tenant system $102_1$ within the multi-tenant server 104. In response, a transaction queue 104A may generate a transaction object corresponding to the record in the shadow object using the exchange object of the peer-to-peer blockchain network 108 and a set of cryptographic keys of the tenant system $102_1$ such that the transaction object may be distributed or otherwise be made available to virtual spaces/organizations of the other tenant system $102_2$ and $102_3$. The virtual spaces/organizations of the other tenant systems $102_2$ and $102_3$ may thereafter analyze the transaction object to determine whether validation/verification is appropriate.

The transaction queue 104A may wait for validation/verification from the virtual spaces/organizations of the tenant systems $102_2$ and $102_3$ such that consensus for the proposed alteration to the physical object of the tenant system $102_1$ is achieved. In response to this consensus, a virtual space/organization of a leader tenant system 102 may (1) add a record or modify a record (as appropriate) in a corresponding physical object of this leader tenant system 102 and (2) add a corresponding entry/block to a distributed ledger of this leader tenant system 102. Thereafter, the virtual space/organization of a leader tenant system 102 may transmit a request to the virtual spaces/organizations of the other/remaining tenant systems 102 to commit the change to their physical objects (based on a mapping defined in the exchange object) and/or add a corresponding entry/block to a ledger of these other/remaining tenant systems 102.

As will be described in greater detail below, each of the tenant systems $102_1$-$102_3$ may initiate a smart contract by initiating a transaction in the blockchain network 108 via a corresponding transaction generator $110_1$-$110_3$. The smart contract may include a set of conditions and a set of operations to perform in response to one or more conditions in the set of conditions being met. For example, the set of conditions may include authorization from a patient to share/distribute medical records of the patient in the peer-to-peer blockchain network 108. In this example, an associated operation for this condition, which would be performed when the condition is True (i.e., authorization is provided by a patient to share/distribute medical records of the patient in the peer-to-peer blockchain network 108) would be the sharing/distribution of medical records of the patient to the tenant systems 102 in the peer-to-peer blockchain network 108. In some implementations, smart contracts may operate across multiple objects in the peer-to-peer blockchain network 108. For example, a first physical object may correspond to patients (e.g., the first physical object associated with the tenant system $102_1$ includes a set of patient records and a set of fields, which describe the name, address, patient identifier, and an indication as to whether patient medical records are authorized for sharing/distribution) and a second physical object may correspond to patient medical records (e.g., a second physical object associated with the tenant system $102_2$ includes a set of patient medical records and a set of fields, which describe the patient identifier associated with a record, a physician identifier, and details regarding the results of a set of medical tests). Using the example smart contract described above in which the set of conditions include authorization from a patient to share/distribute medical records of the patient and an associated operation for this condition is sharing/distributing medical records of the patient in the peer-to-peer blockchain network 108, upon the smart contract manager 112 determining that a patient record in the first physical object includes authorization to share/distribute medical records, the smart contract manager 112 may initiate a transaction in the peer-to-peer blockchain network 108 corresponding to the patient medical record in the second physical object. Accordingly, the smart contract in this example operates across two separate objects that are associated with separate tenants/peers.

As illustrated above and as will be described in greater detail below, the cloud environment/system provided by the multi-tenant server 104 (e.g., the virtual spaces/organizations provided by the multi-tenant server 104) may be used for managing blockchain transactions between the tenant systems $102_1$-$102_3$. Accordingly, the cloud environment/system implemented by the multi-tenant server 104 provides the same level of security, trust, and immutability of information as a blockchain network during inter-tenant communications while centralizing functionality/operations of the peer-to-peer blockchain network 108. Further, the computing environment 100, including the multi-tenant server 104, implements the peer-to-peer blockchain network 108 to allow use of smart contracts as described herein.

Each element of the computing environment 100 of FIG. 1 will now be described in greater detail below by way of example. In some implementations, the computing environment 100 may include more elements than those shown in FIG. 1. Accordingly, the computing environment 100 of FIG. 1 is purely for illustrative purposes.

As shown in FIG. 1 and described above, the tenant systems $102_1$-$102_3$ and the multi-tenant server 104 may be connected through a set of one or more communication networks 106. The set of one or more communication networks 106 may be, for example, a local area network (LAN), a wide area network (WAN), a global area network (GAN), such as the Internet, or a combination of such networks. In another implementation, the tenant systems $102_1$-$102_3$ and the multi-tenant server 104 may maintain a direct connection to each other via a wired or wireless medium.

Each of the tenant systems $102_1$-$102_3$ may be a computing system that may be operated by one or more users. For example, each of the tenant systems $102_1$-$102_3$ may be a personal computer (PC), a workstation, a laptop computer, a tablet computer, a mobile phone, a smartphone, a personal digital assistant (PDA), or the like. As will be described in greater detail below, the tenant systems $102_1$-$102_3$ may communicate with the multi-tenant server 104 to modify/add/store and retrieve data.

The tenant systems $102_1$-$102_3$ (sometimes referred to as client, peer, or user systems) may each include a screen/display (e.g., a liquid crystal (LCD) display) for presenting an interface (e.g., a graphical user interface (GUI)) to a user, including an interface presented in a web page. As will be described in greater detail below, each of the tenant systems $102_1$-$102_3$ may include a corresponding transaction generator 110 for receiving inputs from a user (e.g., via a user interface) to alter a physical object (e.g., addition of a new record in the physical object or modification of an existing record in the physical object) or adding/updating a smart contract in the peer-to-peer blockchain network.

The tenant systems $102_1$-$102_3$ may each be associated with one or more organizations/tenants that are managed by the multi-tenant server 104. For example, users of the tenant system $102_1$ may be customers of a first organization/tenant and a user of the tenant system $102_2$ may be a customer of a second organization/tenant. Organizations/tenants may be any firm, corporation, institution, association, or society that has contracted with an administrator of the multi-tenant server 104 to provide users access to data stored therein via the tenant systems $102_1$-$102_3$.

In one implementation, the multi-tenant server 104 may be any computing device that provides users access to resources via the tenant systems $102_1$-$102_3$ and the communication network(s) 106. For example, the multi-tenant server 104 may provide users of the tenant systems $102_1$-$102_3$ access to data in one or more physical objects and/or one or more corresponding distributed peer ledgers that describe changes to physical objects. For instance, a physical object of the tenant system $102_1$ may correspond to a medical lab report. In this example implementation, the records in the physical object may include a lab report identifier field, a patient name field, a lab network identifier field, a lab test identifier field, a patient identifier field, a social security number field, and a distribution field, which indicates when a patient has authorized the sharing/distribution of medical records of the patient in the peer-to-peer blockchain network 108. When an alteration/change is desired to a physical object of a tenant system 102 (e.g., addition of a new record to a physical object or modification of an existing record in a physical object), the multi-tenant server 104 uses the transaction queue 104A, the tenant level objects 104B, the network level objects 104C, and the blockchain services 104D to attempt to make these alterations in the peer-to-peer blockchain network 108 (e.g., alterations reflected in physical objects and distributed ledgers associated with the tenant systems $102_1$-$102_3$).

The multi-tenant server 104 may include various elements of hardware and software of a multi-tenant system. As used herein, the term "multi-tenant system" refers to those systems in which various elements of hardware and software may be shared by one or more tenants. For example, the multi-tenant server 104 may simultaneously process requests for a great number of tenants, and a given database table may store records for a potentially much greater number of tenants. The multi-tenant server 104 may include an application platform including a framework (e.g., services and metadata) that allows applications to execute, such as the hardware or software infrastructure of the system. In one implementation, the multi-tenant server 104 includes separate virtual spaces/organizations (sometimes referred to as as portions or partitions) for data/objects as well as services of each tenant system $102_1$-$102_3$. For example, each tenant system $102_1$-$102_3$ may be assigned a separate virtual space/organization. Each virtual space/organization is a logical partition within the multi-tenant server 104 and includes separate tenant level objects 104B that are only accessible to that tenant system 102 and are inaccessible to other tenant systems 102 (e.g., tenant systems 102 cannot read and/or write tenant level objects 104B of another tenant system 102) in addition to services used by the multi-tenant server 104 on behalf of the corresponding tenant system 102 (e.g., blockchain services 104D).

Turning now to FIG. 2, a method 200 according to some implementations will be described for the multi-tenant server 104 to manage data in the peer-to-peer blockchain network 108. In particular, the multi-tenant cloud environment provided by the multi-tenant server 104 may be used for managing smart contracts in the peer-to-peer blockchain network 108. In some implementations, as will be described in greater detail below, smart contracts may span/operate across multiple physical objects in the peer-to-peer blockchain network 108 and may be modified by consensus in the peer-to-peer blockchain network 108.

Figure 3A:
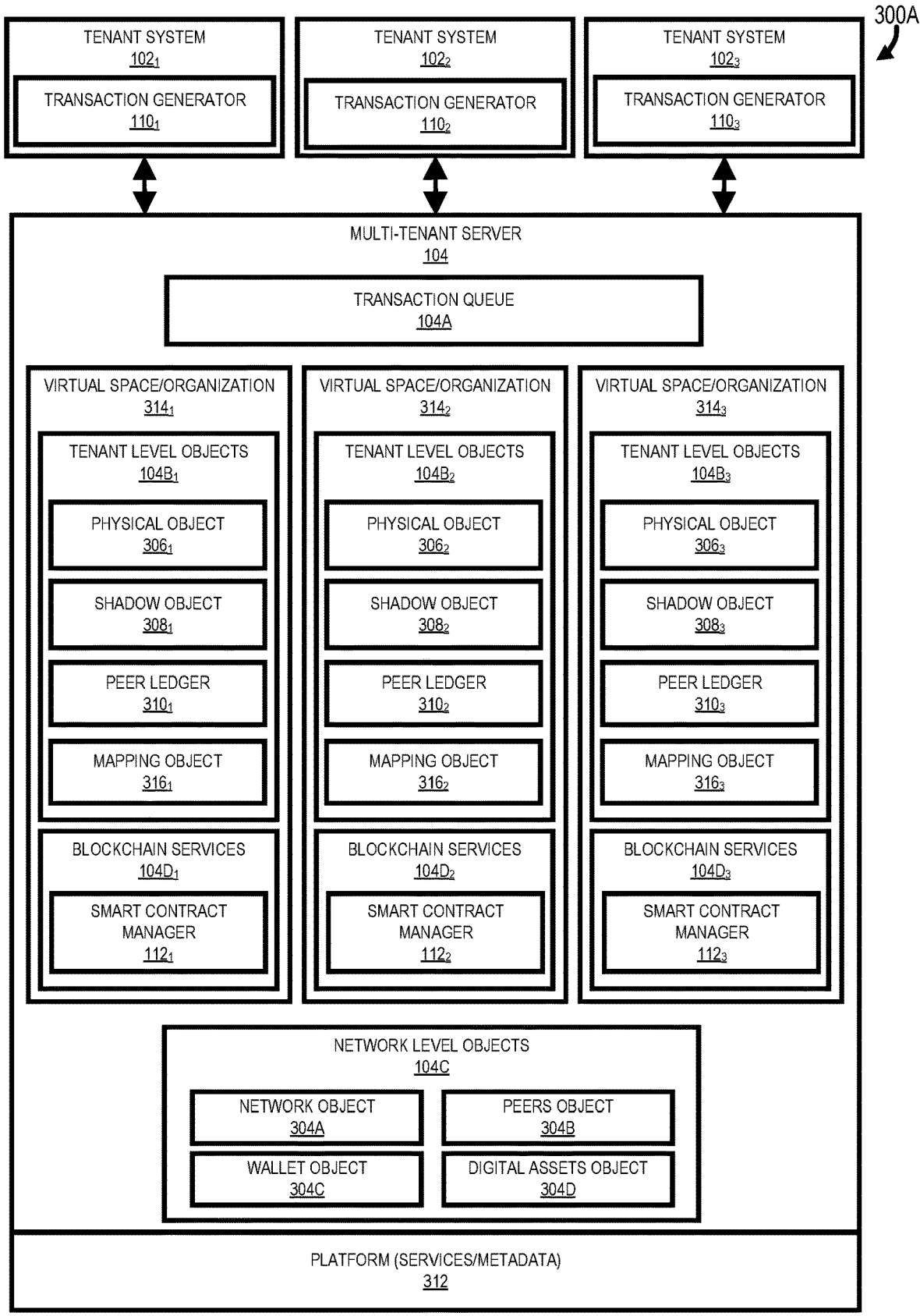
FIG. 3A shows the computing environment, including a set of separate blockchain services per tenant system, according to one example implementation.
Figure 3B:
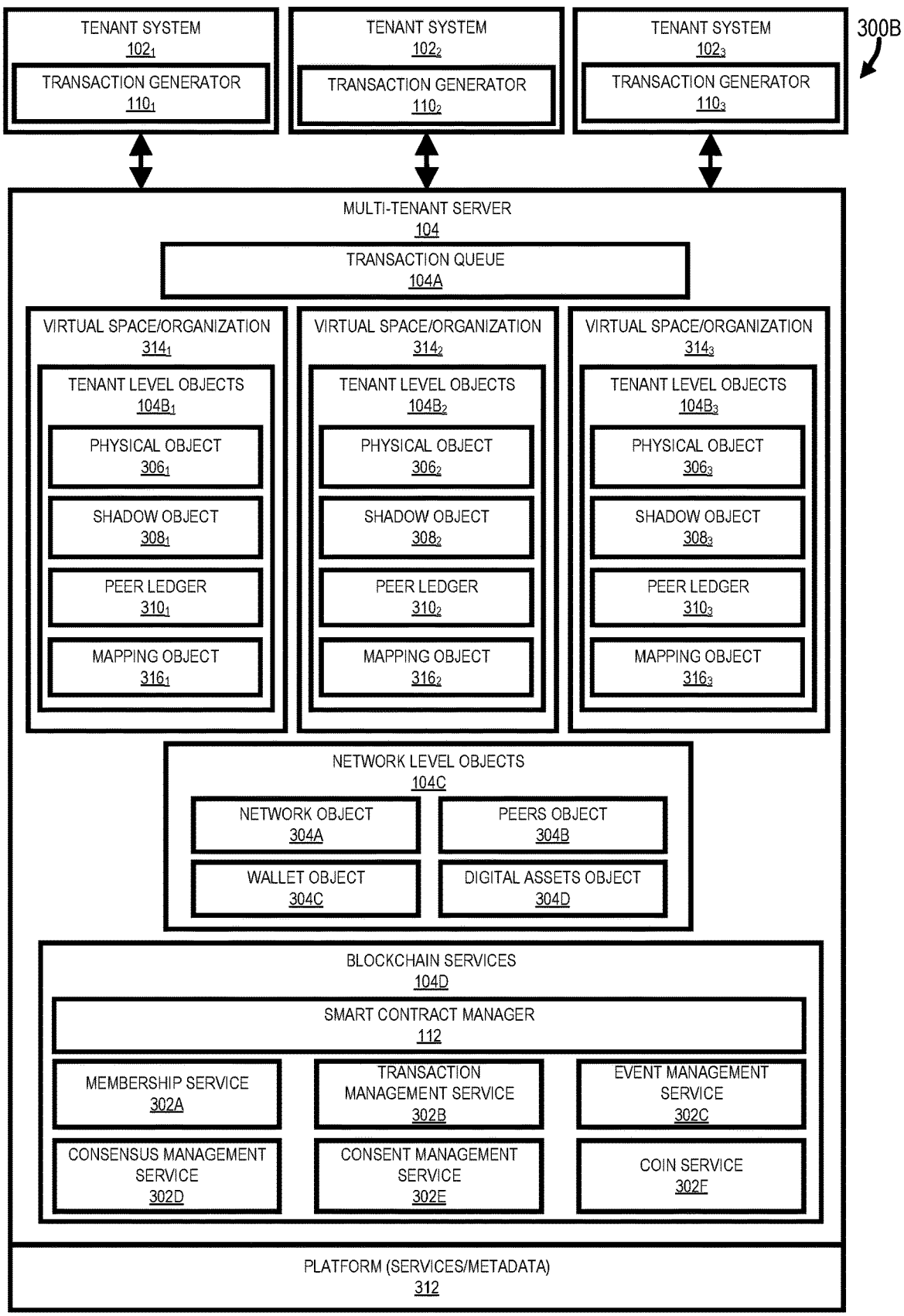
FIG. 3B shows the computing environment, including a set of shared blockchain services, according to another example implementation.

The method 200 will be described in relation to the example computing environment 100 shown in FIG. 1, the example computing environment 300A shown in FIG. 3A, and/or the example computing environment 300B shown in FIG. 3B. However, in other implementations, the method 200 may operate in other environments, including different implementations of the multi-tenant server 104.

As noted above, the operations in the flow diagram of FIG. 2 will be described with reference to the exemplary implementations of the other figures. However, it should be understood that the operations of the flow diagram can be performed by implementations other than those discussed with reference to the other figures, and the implementations discussed with reference to these other figures can perform operations different than those discussed with reference to the flow diagrams.

Although described and shown in FIG. 2 in a particular order, the operations of the method 200 are not restricted to this order. For example, one or more of the operations of the method 200 may be performed in a different order or in partially or fully overlapping time periods. Accordingly, the description and depiction of the method 200 is for illustrative purposes and is not intended to restrict to a particular implementation.

As shown in FIG. 2, the method 200 may commence at operation 202 with the membership service 302A of the blockchain services 104D determining and/or adding a set of tenants (sometimes referred to as peers) to the peer-to-peer blockchain network 108. In some implementations, the peer-to-peer blockchain network 108 is identified in the network object 304A and the tenants for the peer-to-peer blockchain network 108 are identified in the peers object 304B (e.g., tenants represented by identifiers of the tenant system $102_1$-$102_3$). For example, the membership service 302A may determine a set of tenants in the peer-to-peer blockchain network 108 by examining the peers object 304B at operation 202. In some implementations, adding a tenant/tenant system $102_1$-$102_3$ to the peer-to-peer blockchain network 108 may require consensus through a process of verification/validation from the current tenants/tenant systems $102_1$-$102_3$ in the peer-to-peer blockchain network 108. In the example computing environment 100 of FIG. 1, the example computing environment 300A of FIG. 3A, and the example computing environment 300B of FIG. 3B and for purposes of illustrating the method 200 hereinafter, the membership service 302A determines at operation 202 that the peer-to-peer blockchain network 108 includes the tenant systems $102_1$-$102_3$, which represent tenants/peers.

As noted above, each of the tenant systems $102_1$-$102_3$ may include a separate virtual space/organization within the multi-tenant server 104. Each virtual space/organization includes separate tenant level objects 104B that are only accessible to that tenant system $102_1$-$102_3$ and are inaccessible to other tenant systems $102_1$-$102_3$ (e.g., tenant systems $102_1$-$102_3$ cannot read and/or write tenant level objects 104B of another tenant system $102_1$-$102_3$), in addition to services used by the multi-tenant server 104 on behalf of the corresponding tenant systems $102_1$-$102_3$ (e.g., blockchain services 104D). For example, as shown in FIG. 3A, each tenant system $102_1$-$102_3$ may be associated with a separate virtual space/organization $314_1$-$314_3$ with corresponding tenant level objects $104B_1$-$104B_3$ (e.g., physical objects $306_1$-$306_3$, shadow objects $308_1$-$308_3$, peer ledgers $310_1$-$310_3$, and mapping objects $316_1$-$316_3$) and blockchain services $104D_1$-$104D_3$, including corresponding smart contract managers $112_1$-$112_3$. Although shown in FIG. 3A as separate instantiations of the blockchain services $104D_1$-$104D_3$ for each virtual space/organization $314_1$-$314_3$, each virtual space/organization $314_1$-$314_3$ may instead have separate access to a single instantiation of the blockchain services 104D as shown in FIG. 3B.

At operation 204, the membership service 302A may generate a set of public keys (PKs) and private/secret keys (SKs) for each tenant/tenant system $102_1$-$102_3$ in the peer-to-peer blockchain network 108. In one implementation, the public keys are generated based on a determined private key. For example, a one-way cryptographic hash function (e.g., SHA256) may be used to generate public keys for the tenant systems $102_1$-$102_3$ based on corresponding private keys. In one implementation, the public keys and the private/secret keys may be stored by the membership service 302A in the wallet object 304C following generation at operation 204. As will be described in greater detail below, the transaction queue 104A may utilize the private/secret keys stored in the wallet object 304C for generating transaction objects for each of the tenant systems $102_1$-$102_3$. In particular, the private/secret keys may be used by the transaction queue 104A for implementing cryptographic elements of transactions used by the peer-to-peer blockchain network 108.

Figure 4:
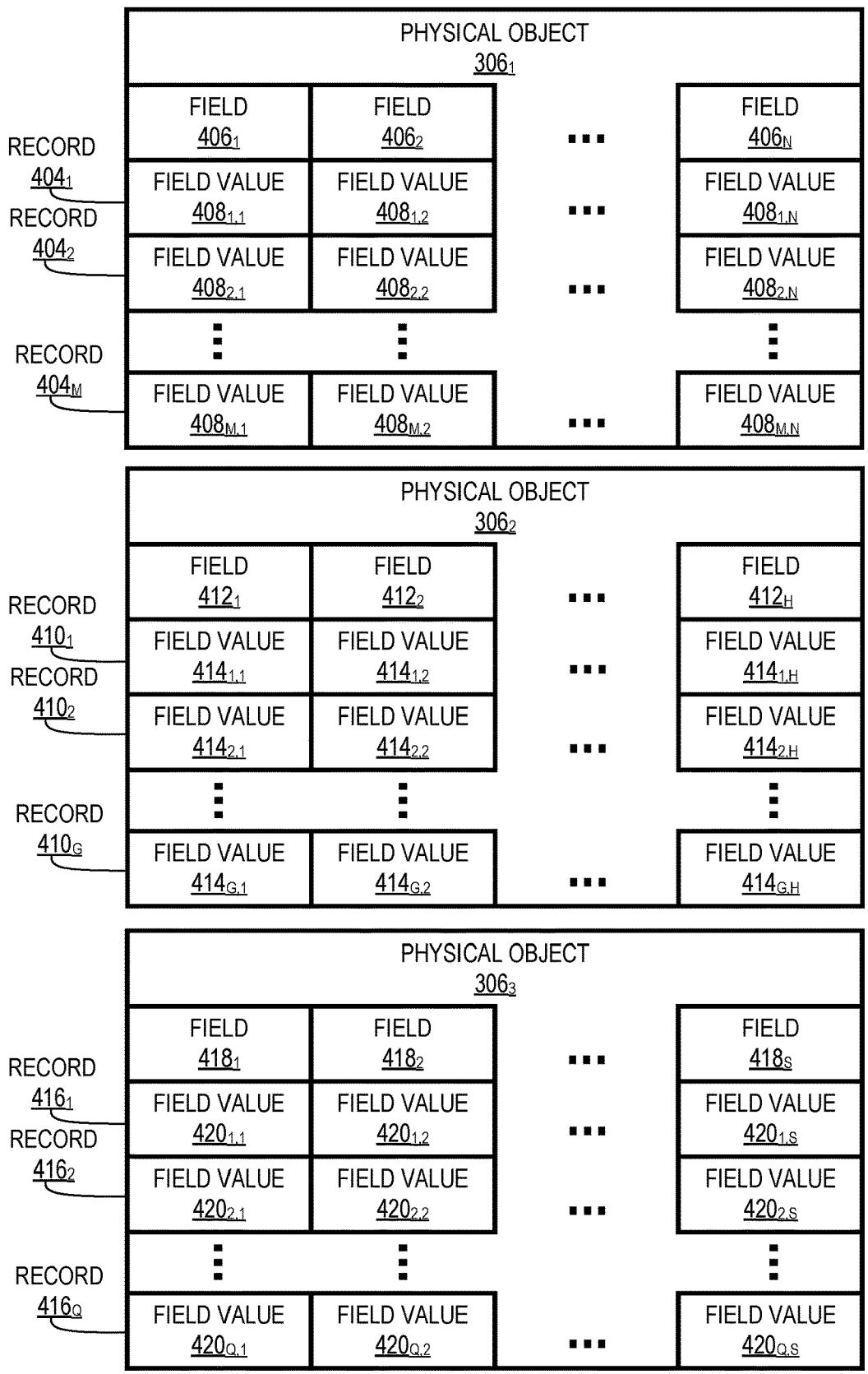
FIG. 4 shows physical objects corresponding to a set of tenant systems, according to one example implementation.

At operation 206, the membership service 302A may determine an exchange object for the peer-to-peer blockchain network 108. In one implementation, the exchange object is defined by a set of exchange fields and mapping metadata that defines mappings between each exchange field and fields in physical objects of the tenant systems $102_1$-$102_3$. For example, FIG. 4 shows physical objects $306_1$-$306_3$ for the tenant systems $102_1$-$102_3$, respectively. In this example, the physical object $306_1$, corresponding to the tenant system $102_1$, includes records $404_1$-$404_M$, which are composed of fields $406_1$-$406_N$, and each record $404_1$-$404_M$ includes values $408_{1,1\text{-}M,N}$ for each field $406_1$-$406_N$. Similarly, the physical object $306_2$, corresponding to the tenant system $102_2$, includes records $410_1$-$410_G$, which are composed of fields $412_1$-$412_H$, and each record $410_1$-$410_G$ includes values $414_{1,1\text{-}G,H}$ for each field $412_1$-$412_H$. Likewise, the physical object $306_3$, corresponding to the tenant system $102_3$, includes records $416_1$-$416_Q$, which are composed of fields $418_1$-$418_S$, and each record $416_1$-$416_Q$ includes values $420_{1,1\text{-}Q,S}$ for each field $418_1$-$418_S$. Each of the physical objects $306_1$-$306_3$ may represent any type of data. For example, the tenant system $102_1$ may operate in or otherwise correspond to a medical laboratory. In this example, the physical object $306_1$ may represent medical lab reports (e.g., each of the records $404_1$-$404_M$ may correspond to separate medical lab reports). The tenant system $102_2$ may operate in or otherwise correspond to a doctor's office. In this example, the physical object $306_2$ may represent a patient file (e.g., each of the records $410_1$-$410_G$ may correspond to separate patient files).

Figure 5:
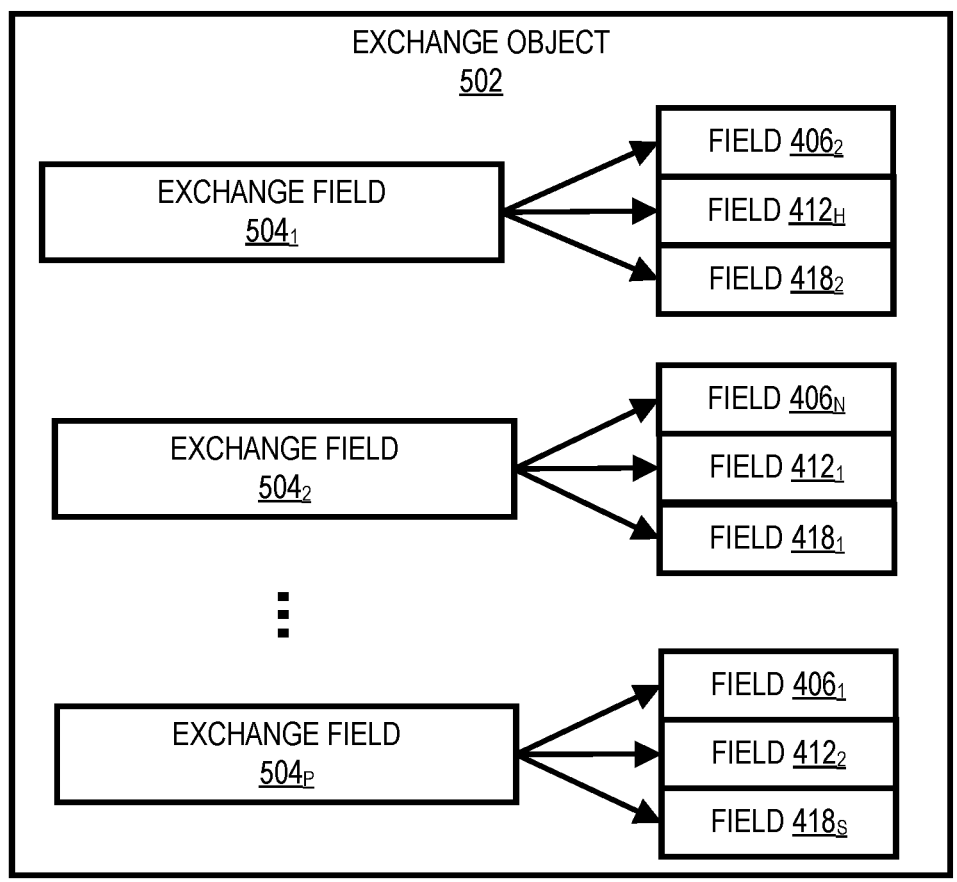
FIG. 5 shows an exchange object, including a set of mappings between exchange fields and fields of physical objects, according to one example implementation.

For the example physical objects $306_1$-$306_3$ shown in FIG. 4, the membership service 302A may determine an exchange object 502 as shown in FIG. 5, which may be stored in the digital assets object 304D. As shown in FIG. 5, the exchange object 502 is defined by the exchange fields $504_1$-$504_P$ and the mapping metadata that maps exchange fields 504 to fields of physical objects 306. In this configuration, the exchange field $504_1$ maps to the field $406_2$ of the physical object $306_1$, the field $412_H$ of the physical object $306_2$, and the field $418_2$ of the physical object $306_3$. The exchange field $504_2$ maps to the field $406_N$ of the physical object $306_1$, the field $412_1$ of the physical object $306_2$, and the field $418_1$ of the physical object $306_3$. The exchange field $504_P$ maps to the field $406_1$ of the physical object $306_1$, the field $412_2$ of the physical object $306_2$, and the field $418_S$ of the physical object $306_3$. Accordingly, the mapping metadata of the exchange object 502 maps/links exchange fields 504 to fields of physical objects 306. In some implementations, the number of exchange fields $504_1$-$504_P$ (i.e., P) is less than (1) the number of fields $406_1$-$406_N$ in the physical object $306_1$ (i.e., N), (2) the number of fields $412_1$-$412_H$ in the physical object $306_2$ (i.e., H), and/or (3) the number of fields $418_1$-$418_S$ in the physical object $306_3$ (i.e., S). Accordingly, a generated transaction object, which will be distributed amongst the tenant systems $102_1$-$102_3$, and corresponding data/information included in distributed peer ledgers 310 may not include sensitive data.

The mapping of exchange fields 504 to fields 406, 412, and 418 of physical objects $306_1$-$306_3$ indicates a relationship between the fields 406, 412, and 418 of physical objects $306_1$-$306_3$. For instance, using the example above in which the physical object $306_1$ represents medical lab reports and the physical object $306_2$ represents patient files, the field $406_2$ of the physical object $306_1$ may correspond to a patient identifier for which a corresponding medical lab report was generated and the field $412_H$ of the physical object $306_2$ may correspond to a patient identifier for which a corresponding patient file represents. As shown in FIG. 5 and described above, these fields $406_2$ and $412_H$ are mapped to the same exchange field $504_1$, indicating that these fields $406_2$ and $412_H$ represent similar data (e.g., the fields $406_2$ and $412_H$ both represent patient identifiers).

In some implementations, each tenant/tenant system $102_1$-$102_3$ may be part of multiple blockchain networks, including the blockchain network 108. Each of these blockchain networks may include overlapping membership with the blockchain network 108 and/or may include additional peers/tenant systems 102. In some implementations, the network object 304A may include identifiers for each blockchain network managed by the multi-tenant server 104, the peers object 304B may include identifiers for each peer/tenant system 102 in the blockchain networks managed by the multi-tenant server 104, the wallet object 304C may include keys for each peer/tenant system 102 in the blockchain networks managed by the multi-tenant server 104, and the digital assets object 304D may include exchange objects 502 for each blockchain network managed by the multi-tenant server 104. In some implementations, the tenant level objects 104B for each tenant system 102 may include a mapping object 316. Each mapping object 316 includes the mapping metadata for the corresponding tenant system 102. For example, the mapping object $316_1$, which corresponds to the tenant system $102_1$, includes mapping metadata that maps exchange field $504_1$ to field $406_2$ of the physical object $306_1$; exchange field $504_2$ to field $406_N$ of the physical object $306_1$; and exchange field $504_P$ to field $406_1$ of the physical object $306_1$. In contrast, the mapping object $316_2$, which corresponds to the tenant system $102_2$, includes mapping metadata that maps exchange field $504_1$ to field $412_H$ of the physical object $306_2$; exchange field $504_2$ to field $412_1$ of the physical object $306_2$; and exchange field $504_P$ to field $412_2$ of the physical object $306_2$. Lastly, the mapping object $316_3$, which corresponds to the tenant system $102_3$, includes mapping metadata that maps exchange field $504_1$ to field $418_2$ of the physical object $306_3$; exchange field $504_2$ to field $418_1$ of the physical object $306_3$; and exchange field $504_P$ to field $418_S$ of the physical object $306_3$. Accordingly, each mapping object 316 only includes mapping metadata associated with a corresponding tenant system 102.

At operation 208, a smart contract manager 112 receives a smart contract request for establishing a smart contract in the peer-to-peer blockchain network 108. In one embodiment, the smart contract request is received from a tenant system 102 and defines a smart contract for use in the peer-to-peer blockchain network 108. For example, the smart contract may include a set of conditions and a set of operations to perform in response to one or more conditions in the set of conditions being met. For instance, the set of conditions may include authorization from a patient to share/distribute medical records of the patient in the peer-to-peer blockchain network 108. In this example, an associated operation for this condition, which would be performed when the condition is True (i.e., authorization is provided by a patient to share/distribute medical records of the patient) would be the sharing/distribution of medical records of the patient to tenant systems 102 in the peer-to-peer blockchain network 108 (e.g., initiating a transaction to share/distribute associated records in the peer-to-peer blockchain network 108). In some implementations, the smart contract may operate across objects in the blockchain network 108. For example, the physical object $306_1$ may correspond to patient medical records (e.g., the physical object $306_1$ includes a set of patient medical records 404 and a set of fields 406, which describe the patient identifier associated with a record 404, a physician identifier, and details regarding the results of a set of medical tests) and the physical object $306_2$ associated with the tenant system $102_2$ may correspond to patients (e.g., the physical object $306_2$ includes a set of patient records 410 and a set of fields 412, which describe the name, address, patient identifier, and an indication as to whether the corresponding patient medical record 404 is authorized for sharing/distribution in the peer-to-peer blockchain network 108). Using the example smart contract described above in which the set of conditions include authorization from a patient to share/distribute medical records of the patient and an associated operation for this condition is sharing/distribution of medical records of the patient to tenant systems 102 in the peer-to-peer blockchain network 108, upon the smart contract manager 112 determining that a patient record 410 in the physical object $306_2$ includes authorization to share/distribute medical records 404 of the physical object $306_1$, the smart contract manager 112 may initiate a transaction in the peer-to-peer blockchain network 108 corresponding to the patient medical record 404 in the physical object $306_1$. Accordingly, the smart contract in this example operates across two separate physical objects 306 associated/owned by separate tenant systems 102. For purposes of explanation, the method 200 will be described in relation to the smart contract described above.

At operation 210, the smart contract manager 112 may attempt to obtain consensus for the smart contract from tenant systems 102 in the peer-to-peer blockchain network 108. To attempt to obtain consensus for the smart contract, the event management service 302C and/or the transaction queue 104A may make a smart contract object available to tenant systems 102 in the peer-to-peer blockchain network 108. In some implementations, making the smart contract object available to the other tenant systems 102 includes the transaction queue 104A signing the smart contract object using the private key of the tenant system $102_1$ (or similar techniques according to a blockchain protocol) and placing the smart contract object with the applied signature in a portion/partition of the multi-tenant server 104 accessible to the other tenant systems $102_2$ and $102_3$. For example, as described above, the multi-tenant server 104 may include a separate virtual space/organization 314 for each of the tenant systems 102. Each virtual space/organization 314 includes data and services that are only accessible to that tenant system 102 and is inaccessible to other tenant systems 102. For example, the multi-tenant server 104 may pass the smart contract object from the virtual space/organization $314_1$ of the tenant system $102_1$, from which the initial smart contract request was received, to the virtual spaces/organizations $314_2$ and $314_3$ of the tenant systems $102_2$ and $102_3$ such that the virtual spaces/organizations $314_2$ and $314_3$ of the tenant systems $102_2$ and $102_3$ can process/analyze the smart contract object for possible validation/verification.

At operation 212, the transaction management service 302B may monitor responses from the tenant systems $102_2$ and $102_3$ to determine if consensus has been reached regarding the smart contract or if consensus has failed to be reached. In one implementation, the consensus management service 302D may define the threshold or rules for use by the transaction management service 302B in determining when consensus has been reached by the tenant systems $102_2$ and $102_3$ regarding the smart contract. For example, in some implementations, the consensus management service 302D may indicate that consensus requires all of the tenant systems $102_2$ and $102_3$ to verify/validate the smart contract, while in other implementations, the consensus management service 302D may indicate that consensus requires a majority of the tenant systems $102_2$ and $102_3$ to verify/validate the smart contract. In some implementations, the consent management service 302E indicates the rules and/or operations used by the tenant systems $102_2$ and $102_3$, and in particular the virtual spaces/organizations $314_2$ and $314_3$ associated with the tenant systems $102_2$ and $102_3$, to determine if verification/validation of the smart contract is proper. For example, the consent management service 302E may indicate that the public key of the tenant system $102_1$ is used along with the signature and smart contract object for determining whether the smart contract object originated from and was authorized by the tenant system $102_1$.

At operation 214, the transaction management service 302B and the transaction queue 104A may discard the smart contract object in response to failing to obtain consensus from the tenant systems $102_2$ and $102_3$ (e.g., failing to obtain consensus as defined/indicated by the consensus management service 302D). In some implementations, discarding the smart contract object may include indicating to the tenant system $102_1$, which transmitted/generated the initial smart contract request, that the smart contract has been rejected by the peer-to-peer blockchain network 108 (i.e., consensus in the peer-to-peer blockchain network 108 was not achieved/obtained).

Figure 8:
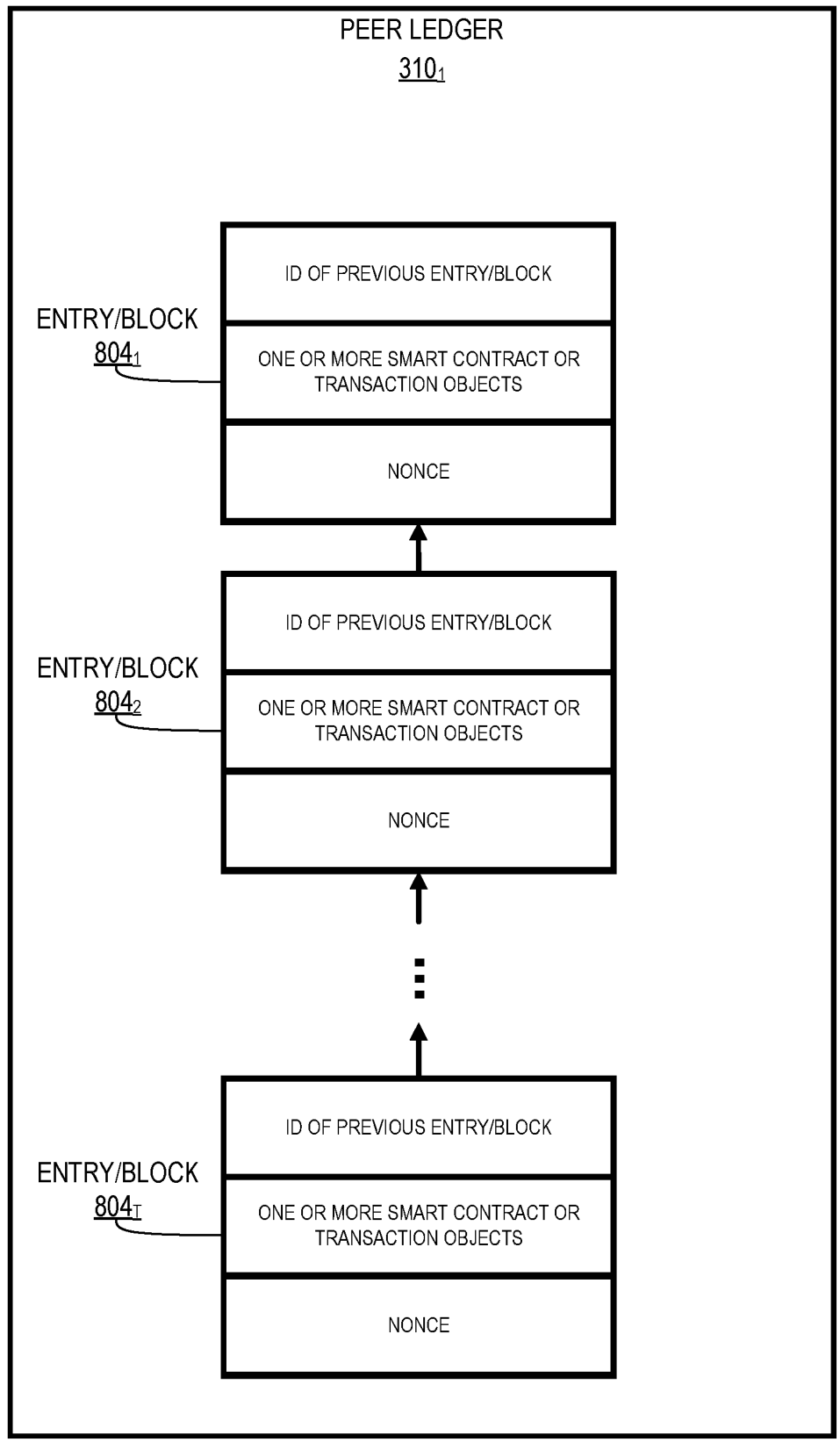
FIG. 8 shows an example of a blockchain, including a set of entries/blocks, according to one example implementation.

At operation 216, the transaction management service 302B may commit the smart contract object for which consensus was achieved on behalf of a leader tenant system 102. In some implementations, the transaction management service 302B may add an entry/block in the peer ledger 310 corresponding to the smart contract object on behalf of a leader tenant system 102. In particular, the transaction management service 302B of the virtual space/organization 314 of a leader tenant system 102 may add an entry/block in the peer ledger 310 corresponding to the smart contract object on behalf the leader tenant system 102. The entry/block added to the peer ledger 310 may include several pieces of information. For example, as shown in FIG. 8, each entry/block $804_1$-$804_T$ in the peer ledger $310_1$ may include a reference to the previous entry/block 804 in the peer ledger $802_1$, the smart contract object (along with one or more other objects), and a nonce (i.e., an arbitrary number used to meet a requirement of the peer-to-peer blockchain network 108).

At operation 218, the transaction management service 302B and/or the transaction queue 104A may commit the smart contract object for which consensus was achieved on behalf of the remaining tenant systems 102. In some implementations, committing the smart contract object by the remaining tenant systems 102 may include the leader tenant system 102 transmitting a request or otherwise triggering the remaining tenant systems 102 to commit the smart contract object for which consensus was achieved. In particular, the transaction management service 302B of the virtual space/organization $314_1$-$314_3$ of the leader tenant system $102_1$-$102_3$ passes or otherwise makes available a request or otherwise triggers the transaction management service 302B of the virtual spaces/organizations $314_1$-$314_3$ of the remaining tenant systems $102_1$-$102_3$ to add a block/entry to corresponding peer ledgers $310_1$-$310_3$. The peer ledgers $310_1$-$310_3$ allow the computing environments 100, 300A, and/or 300B to maintain the transparency and auditability of data. In particular, the multi-tenant server 104 provides immutability to each transaction by recording/reflecting the transaction in the peer ledgers $310_1$-$310_3$, which are replicated across all the tenant systems $102_1$-$102_3$. As described above, the tenant systems $102_1$-$102_3$ participate in a consensus mechanism to verify/validate transactions/smart contract objects and only after the transactions/smart contract objects are verified/validated will the transactions/smart contract objects be committed to the peer ledgers $310_1$-$310_3$. In some implementations, the peer ledgers $310_1$-$310_3$ may be stored in a Merkle directed acyclic graph (DAG) structure. The Merkle DAG may be represented in an Oracle and/or HBase store.

Although operations 208-216 are described as being performed in relation to the addition of a smart contract to the peer-to-peer blockchain network 108, in some implementations, the operations 208-216 may similarly function to alter a smart contract in the peer-to-peer blockchain network 108. For example, operations 208-216 may function to provide consensus in the peer-to-peer blockchain network 108 to adding or modifying a condition or an operation of a smart contract already committed/established in the peer-to-peer blockchain network 108.

At operation 220, the smart contract manager 112 may continually monitor and determine whether the set of conditions of the smart contract have been met. For instance, in the example smart contract described above, in response to determining that a patient record 410 in the physical object $306_2$ includes authorization to share/distribute medical records 404 of the physical object $306_1$, the method 200 may move to operation 222. In contrast, in the example smart contract described above, in response to determining that a patient record 410 in the physical object $306_2$ does not include authorization to share/distribute medical records 404 of the physical object $306_1$, the method 200 may remain at operation 220.

At operation 222, the one or more operations associated with the set of conditions, which were determined to be met at operation 220, are performed. In the example smart contract described above, the set of operations may include the smart contract manager 112 initiating a transaction in the peer-to-peer blockchain network 108 corresponding to the patient medical record 404 in the physical object $306_2$. For example, the patient medical record 404 may be shared/distributed in the peer-to-peer blockchain network 108 through a process of consensus as described herein. For example, FIG. 2B shows a set of operations that may be performed at operation 222.

Figure 2B:
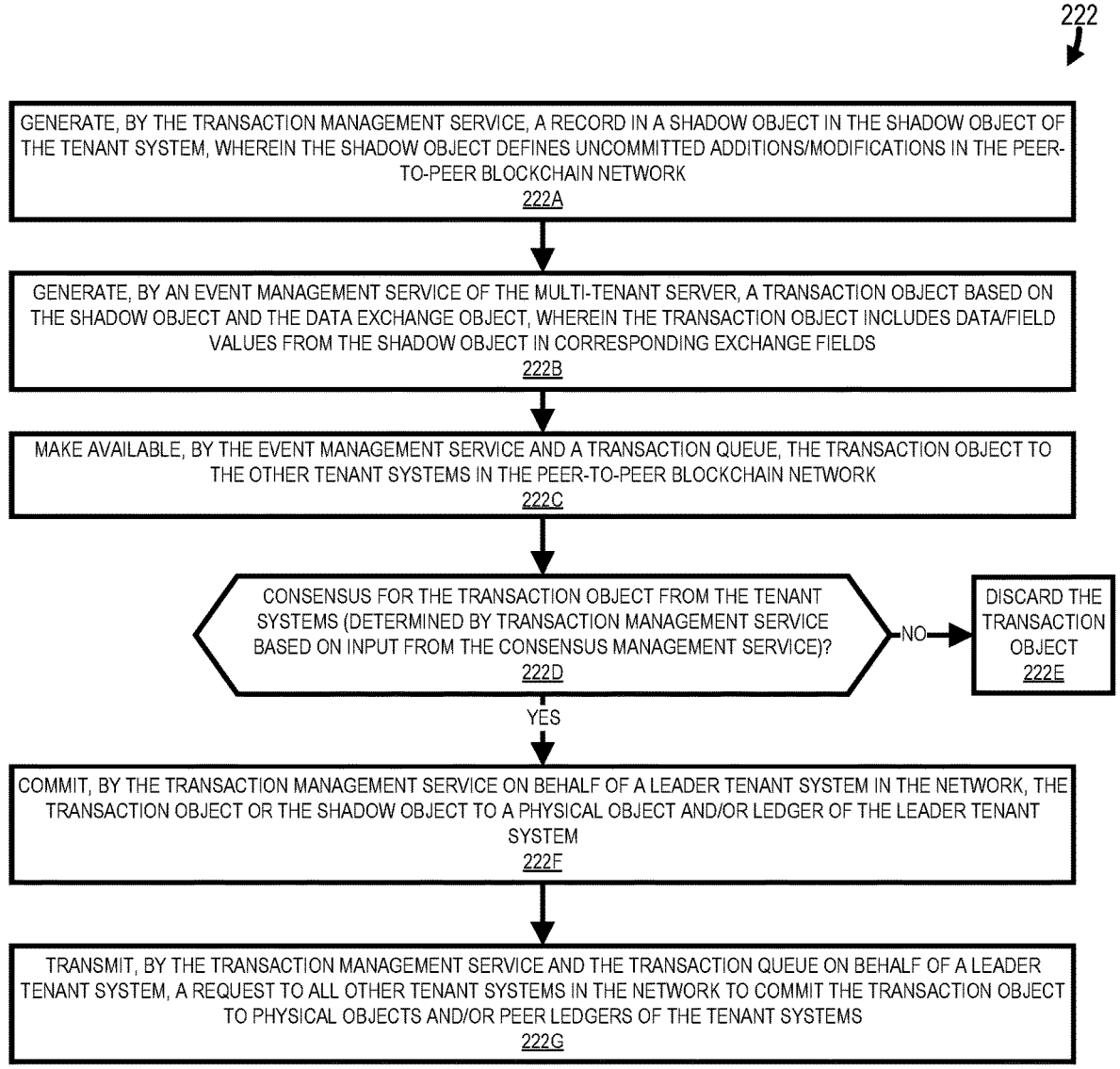

As shown in FIG. 2B, the smart contract manager 112 may cause the transaction management service 302B of the virtual space/organization $314_2$ to generate a record in a shadow object $308_2$ corresponding to a record 410 of the physical object $306_2$ at operation 222A. The shadow object $308_2$ may correspond to the tenant system $102_2$ and may include all the fields $412_1$-$412_H$ of the physical object $306_2$. The shadow object $308_2$ represents un-committed data in the network 108. As will be described in greater detail below, the data in the shadow object $308_2$ of the tenant system $102_2$ needs to be validated/verified through consensus by the other tenant systems 102 before being committed and represented by the peer ledger $310_2$ of the tenant system $102_2$ in addition to being represented by the peer ledgers 310 and physical objects 306 of the other tenant systems 102.

Figure 6:
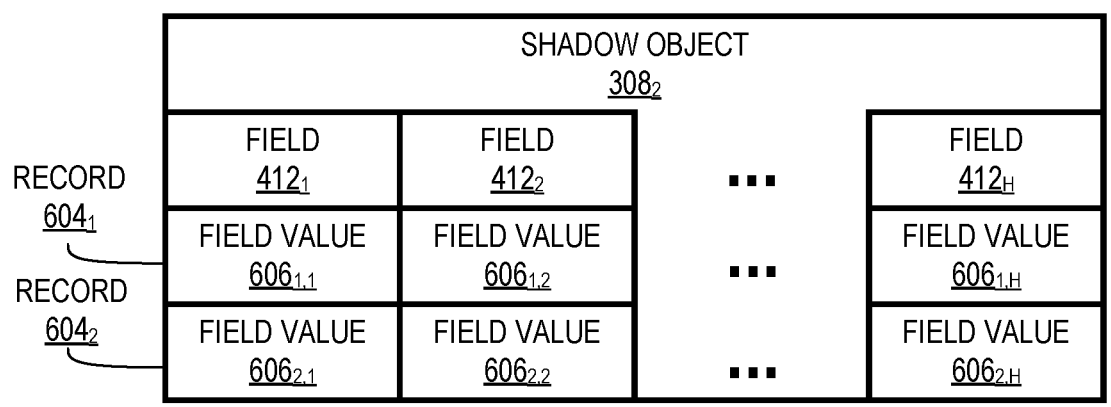
FIG. 6 shows an example of a shadow object corresponding to a tenant system, according to one example implementation.

FIG. 6 shows an example of a shadow object $308_2$ corresponding to the tenant system $102_2$ and the physical object $306_2$, according to one example implementation. As shown, the shadow object $308_2$ includes records $604_1$ and $604_2$, corresponding to uncommitted data. For instance, the record $604_1$ may propose committal of a record 410 corresponding to a medical lab report to the peer-to-peer blockchain network 108.

At operation 222B, the event management service 302C and/or the transaction queue 104A, may generate a transaction object based on (1) the record 604 added to the shadow object $308_2$ at operation 222A and (2) the exchange object 502 of the peer-to-peer blockchain network 108. In particular, the transaction object may include values for each of the exchange fields $504_1$-$504_P$ and the transaction object includes data/field values from the record 604 in corresponding exchange fields $504_1$-$504_P$. For example, FIG. 7 shows an example of a transaction object 702, according to one example implementation.

As shown in FIG. 7, the transaction object 802 includes all the exchange fields $504_1$-$504_P$ of the exchange object 502 and field values 606 from the record $604_1$ in the shadow object $308_2$ in the appropriate positions based on the mapping between exchange fields $504_1$-$504_P$ and fields 412 of the physical object $306_2$. As will be described below, the transaction object 702, which will be used hereinafter for purposes of illustration, may be passed or otherwise made available to the other tenant systems 102 to determine if there is consensus in the peer-to-peer blockchain network 108 to commit the proposed record 410 (e.g., to verify/validate the transaction object 702).

At operation 222C, the event management service 302C and the transaction queue 104A may make the transaction object 702 available to the other tenant systems $102_1$ and $102_3$. In some implementations, making the transaction object 702 available to the other tenant system $102_1$ and $102_3$ includes the transaction queue 104A signing the transaction object 702 using the private key of the tenant system $102_2$ (or similar techniques according to a blockchain protocol) and placing the transaction object 702 with the applied signature in a portion/partition of the multi-tenant server 104 accessible to the tenant systems $102_1$ and $102_3$. For example, as described above, the multi-tenant server 104 may include a separate virtual space/organization 314 for each of the tenant systems 102. Each virtual space/organization 314 includes data and services that are only accessible to that tenant system 102 and is inaccessible to other tenant systems 102. At operation 223C, the multi-tenant server 104 may pass the transaction object 702 with applied signature from the virtual space/organization $314_2$ of the tenant system $102_2$ to the virtual spaces/organizations $314_1$ and $314_3$ of the tenant systems $102_1$ and the $102_3$ such that the virtual spaces/organizations $314_1$ and $314_3$ of the tenant systems $102_1$ and the $102_3$ can process/analyze the transaction object 702 for possible validation/verification.

At operation 222D, the transaction management service 302B may monitor responses from the tenant systems $102_1$ and the $102_3$ to determine if consensus has been reached regarding the transaction object 702 or if consensus has failed to be reached. In one implementation, the consensus management service 302D may define the threshold or rules for use by the transaction management service 302B in determining when consensus has been reached by the tenant systems $102_1$ and the $102_3$ regarding the transaction object 702. For example, in some implementations, the consensus management service 302D may indicate that consensus requires all of the tenant systems $102_1$ and the $102_3$ to verify/validate the transaction object 702, while in other implementations, the consensus management service 302D may indicate that consensus requires a majority of the tenant systems $102_1$ and the $102_3$ to verify/validate the transaction object 702. In some implementations, the consent management service 302E indicates the rules and/or operations used by the tenant systems $102_1$ and the $102_3$, and in particular the virtual spaces/organizations $314_1$ and $314_3$ associated with the tenant systems $102_1$ and the $102_3$, to determine if verification/validation of the transaction object 702 is proper. For example, the consent management service 302E may indicate that the public key of the tenant system $102_2$ is used along with the signature and the transaction object 702 for determining whether the transaction object 702 originated from and was authorized by the tenant system $102_2$.

At operation 222E, the transaction management service 302B and the transaction queue 104A may discard the transaction object 702 in response to failing to obtain consensus from the tenant systems $102_1$ and the $102_3$ (e.g., failing to obtain consensus as defined/indicated by the consensus management service 302D).

At operation 222F, the transaction management service 302B may commit the transaction object 702 and/or the record 604 in the shadow object $308_2$ corresponding to the transaction object 702 for which consensus was achieved on behalf of a leader tenant system 102. In some implementations, a leader tenant system 102 may be randomly selected from amongst the tenant systems $102_1$-$102_3$ in the peer-to-peer blockchain network 108 by the membership service 302A. Committing the transaction object 702 may include one or more of adding the record 604 to a physical object 306 and adding an entry/block in a peer ledger 310 corresponding to the transaction object 702 on behalf the leader tenant system 102. For example, the transaction management service 302B of the virtual space/organization 314 of the leader tenant system 102 may add an entry/block in the peer ledger 310 corresponding to the transaction object 702 on behalf the leader tenant system 102. The entry/block added to the peer ledger 310 may include several pieces of information. For example, as shown in FIG. 8, each entry/block $804_1$-$804_T$ in the peer ledger $310_1$ may include a reference to the previous entry/block 804 in the peer ledger $310_1$, the transaction object 702 (along with one or more other objects), and a nonce (i.e., an arbitrary number used to meet a requirement of the peer-to-peer blockchain network 108).

At operation 222G, the transaction management service 302B and/or the transaction queue 104A may transmit a request or otherwise trigger the other tenant systems 102 on behalf of the leader tenant system 102 to commit the transaction object 702 to corresponding physical objects 306 and/or add a block/entry to corresponding peer ledgers 310.

As illustrated above, the method 200 allows the multi-tenant server 104 to manage data in the peer-to-peer blockchain network 108 on behalf of the tenant systems $102_1$-$102_3$. In particular, the cloud environment provided by the multi-tenant server 104 may be used for managing blockchain transactions between the tenant systems $102_1$-$102_3$. Accordingly, the method 200 allows a cloud environment to provide the same level of security, trust, and immutability of information as a blockchain network during inter-tenant communications while centralizing functionality/operations of the peer-to-peer blockchain network 108. Further, the computing environment 100, including the multi-tenant server 104, implements the peer-to-peer blockchain network 108 to allow use of smart contracts as described herein, including smart contract that operate across tenant objects and those that must be verified (both the introduction and modifications) by consensus in the peer-to-peer blockchain network 108.

In some implementations, the computing environments 300A and/or 300B may be built on top of a platform 302 comprised of services and/or metadata for implementing the other components of the multi-tenant server 104. In some implementations, the blockchain services 104D may include additional services, such as a coin service 302F for tracking records and items associated with each tenant/peer.

As used above, the term "user" is a generic term referring to an entity (e.g., an individual person) using a system and/or service. A multi-tenant architecture provides each tenant with a dedicated share of a software instance and the ability (typically) to input tenant specific data for user management, tenant-specific functionality, configuration, customizations, non-functional properties, associated applications, etc. Multi-tenancy contrasts with multi-instance architectures, where separate software instances operate on behalf of different tenants. A tenant includes a group of users who share a common access with specific privileges to a software instance providing a service. A tenant may be an organization (e.g., a company, department within a company, etc.). A tenant may have one or more roles relative to a system and/or service. For example, in the context of a customer relationship management (CRM) system or service, a tenant may be a vendor using the CRM system or service to manage information the tenant has regarding one or more customers of the vendor. As another example, in the context of Data as a Service (DAAS), one set of tenants may be vendors providing data and another set of tenants may be customers of different ones or all of the vendors' data. As another example, in the context of Platform as a Service (PAAS), one set of tenants may be third party application developers providing applications/services and another set of tenants may be customers of different ones or all of the third-party application developers. A user may have one or more roles relative to a system and/or service. To provide some examples, a user may be a representative (sometimes referred to as an "end user") of a tenant (e.g., a vendor or customer), a representative (e.g., an administrator) of the company providing the system and/or service, and/or a representative (e.g., a programmer) of a third-party application developer that is creating and maintaining an application(s) on a Platform as a Service (PAAS).

One or more parts of the above implementations may include software and/or a combination of software and hardware. An electronic device (also referred to as a computing device, computer, etc.) includes hardware and software, such as a set of one or more processors coupled to one or more machine-readable storage media (e.g., magnetic disks, optical disks, read only memory (ROM), Flash memory, phase change memory, solid state drives (SSDs)) to store code (which is composed of software instructions and which is sometimes referred to as computer program code or a computer program) for execution on the set of processors and/or to store data. For instance, an electronic device may include non-volatile memory (with slower read/write times, e.g., magnetic disks, optical disks, read only memory (ROM), Flash memory, phase change memory, SSDs) and volatile memory (e.g., dynamic random access memory (DRAM), static random access memory (SRAM)), where the non-volatile memory persists code/data even when the electronic device is turned off or when power is otherwise removed, and the electronic device copies that part of the code that is to be executed by the set of processors of that electronic device from the non-volatile memory into the volatile memory of that electronic device during operation because volatile memory typically has faster read/write times. As another example, an electronic device may include a non-volatile memory (e.g., phase change memory) that persists code/data when the electronic device is turned off, and that has sufficiently fast read/write times such that, rather than copying the part of the code/data to be executed into volatile memory, the code/data may be provided directly to the set of processors (e.g., loaded into a cache of the set of processors); in other words, this non-volatile memory operates as both long term storage and main memory, and thus the electronic device may have no or only a small amount of volatile memory for main memory. In addition to storing code and/or data on machine-readable storage media, typical electronic devices can transmit code and/or data over one or more machine-readable transmission media (also called a carrier) (e.g., electrical, optical, radio, acoustical or other form of propagated signals—such as carrier waves, infrared signals). For instance, typical electronic devices also include a set of one or more physical network interface(s) to establish network connections (to transmit and/or receive code and/or data using propagating signals) with other electronic devices. Thus, an electronic device may store and transmit (internally and/or with other electronic devices over a network) code and/or data with one or more machine-readable media (also referred to as computer-readable media).

Electronic devices are used for a variety of purposes. For example, an electronic device (sometimes referred to as a server electronic device) may execute code that cause it to operate as one or more servers used to provide a service to another electronic device(s) (sometimes referred to as a client electronic device, a client computing device, or a client device) that executes client software (sometimes referred to as client code or a tenant system) to communicate with the service. The server and client electronic devices may be operated by users respectively in the roles of administrator (also known as an administrative user) and end user.

Figure 9A:
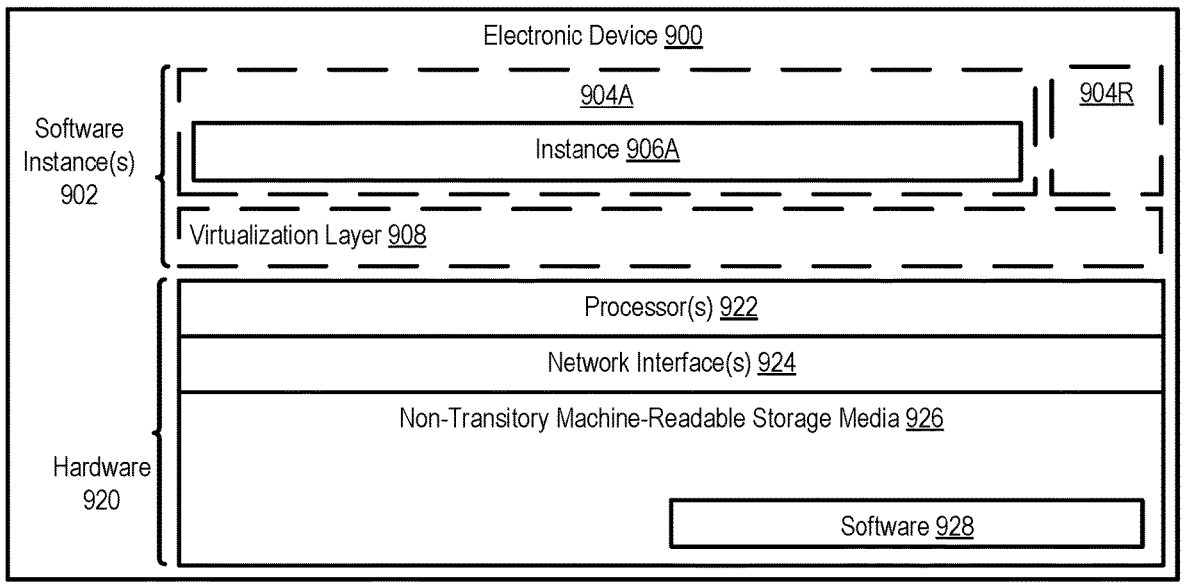
FIG. 9A shows an electronic device according to one example implementation.

FIG. 9A is a block diagram illustrating an electronic device 900 according to some example implementations. FIG. 9A includes hardware 920 comprising a set of one or more processor(s) 922, a set of one or more network interfaces 924 (wireless and/or wired), and non-transitory machine-readable storage media 926 having stored therein software 928 (which includes instructions executable by the set of one or more processor(s) 922). Each of the previously described tenant systems 102 and the transaction queue 104A, the tenant level objects 104B, the network level objects 104C, and the blockchain services 104D may be implemented in one or more electronic devices 900. In one implementation: 1) each of the tenant systems 102 is implemented in a separate one of the electronic devices 900 (e.g., in user electronic devices operated by users where the software 928 represents the software to implement tenant systems 102 to interface with the transaction queue 104A, the tenant level objects 104B, the network level objects 104C, and the blockchain services 104D (e.g., a web browser, a native client, a portal, a command-line interface, and/or an application program interface (API) based upon protocols such as Simple Object Access Protocol (SOAP), Representational State Transfer (REST), etc.)); 2) the transaction queue 104A, the tenant level objects 104B, the network level objects 104C, and the blockchain services 104D are implemented in a separate set of one or more of the electronic devices 900 (e.g., a set of one or more server electronic devices where the software 928 represents the software to implement the transaction queue 104A, the tenant level objects 104B, the network level objects 104C, and the blockchain services 104D); and 3) in operation, the electronic devices implementing the tenant systems 102 and the transaction queue 104A, the tenant level objects 104B, the network level objects 104C, and the blockchain services 104D would be communicatively coupled (e.g., by a network) and would establish between them (or through one or more other layers) connections for submitting a proposed new record or a proposed modification to an existing record in a physical object to the multi-tenant server 104. Other configurations of electronic devices may be used in other implementations (e.g., an implementation in which the tenant systems 102 and the multi-tenant server 104 are implemented on a single electronic device 900).

In electronic devices that use compute virtualization, the set of one or more processor(s) 922 typically execute software to instantiate a virtualization layer 908 and software container(s) 904A-R (e.g., with operating system-level virtualization, the virtualization layer 908 represents the kernel of an operating system (or a shim executing on a base operating system) that allows for the creation of multiple software containers 904A-R (representing separate user space instances and also called virtualization engines, virtual private servers, or jails) that may each be used to execute a set of one or more applications; with full virtualization, the virtualization layer 908 represents a hypervisor (sometimes referred to as a virtual machine monitor (VMM)) or a hypervisor executing on top of a host operating system, and the software containers 904A-R each represent a tightly isolated form of a software container called a virtual machine that is run by the hypervisor and may include a guest operating system; with para-virtualization, an operating system or application running with a virtual machine may be aware of the presence of virtualization for optimization purposes). Again, in electronic devices where compute virtualization is used, during operation an instance of the software 928 (illustrated as instance 906A) is executed within the software container 904A on the virtualization layer 908. In electronic devices where compute virtualization is not used, the instance 906A on top of a host operating system is executed on the "bare metal" electronic device 900. The instantiation of the instance 906A, as well as the virtualization layer 908 and software containers 904A-R if implemented, are collectively referred to as software instance(s) 902.

Alternative implementations of an electronic device may have numerous variations from that described above. For example, customized hardware and/or accelerators might also be used in an electronic device.

A network device (ND) is an electronic device that communicatively interconnects other electronic devices on the network (e.g., other network devices, user electronic devices, server electronic devices). Some network devices are "multiple services network devices" that provide support for multiple networking functions (e.g., routing, bridging, switching, Layer 2 aggregation, session border control, Quality of Service, and/or subscriber management), and/or provide support for multiple application services (e.g., data, voice, and video).

Figure 9B:
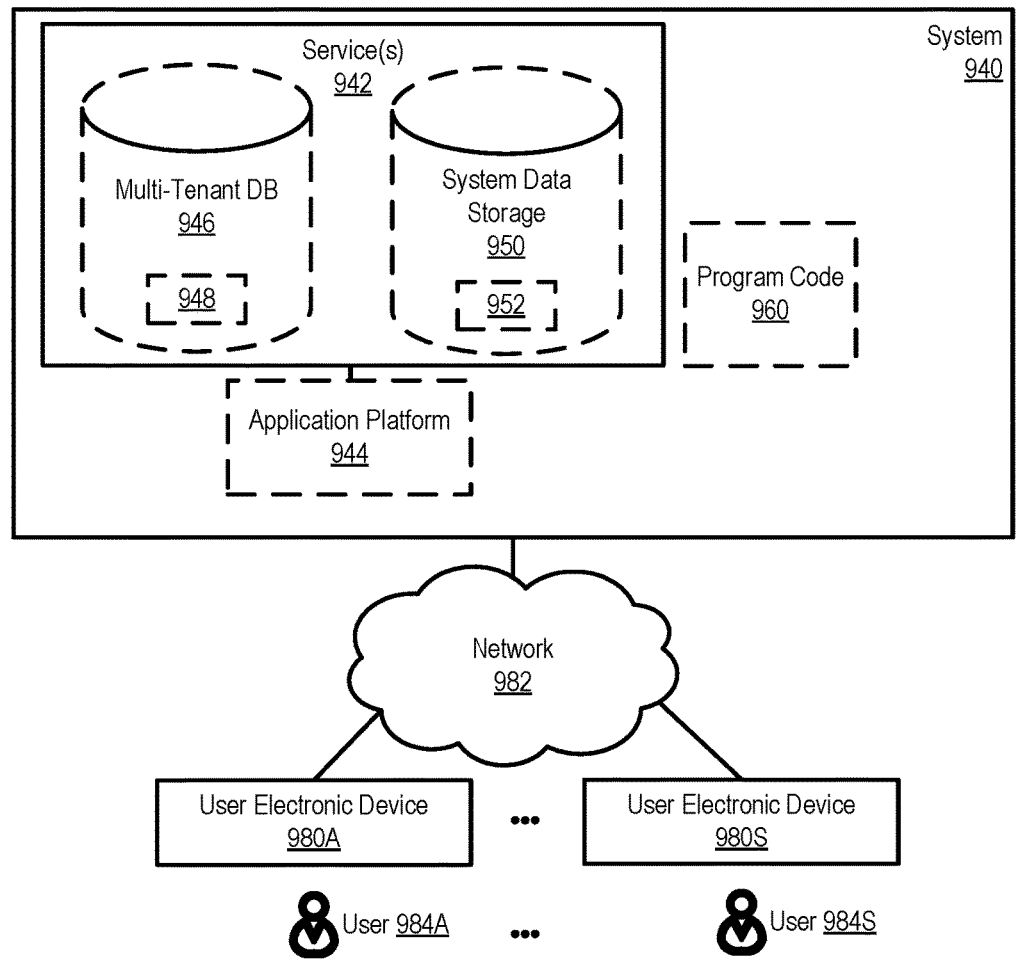
FIG. 9B shows a block diagram of an environment where the computing environment and the server may be implemented according to one example implementation.

FIG. 9B is a block diagram of an environment where the tenant systems $102_1$-$102_3$ and the multi-tenant server 104 may be deployed, according to some implementations. A system 940 includes hardware (a set of one or more electronic devices) and software to provide service(s) 942, including the transaction queue 104A, the tenant level objects 104B, the network level objects 104C, and the blockchain services 104D. The system 940 is coupled to user electronic devices 980A-S over a network 982. The service(s) 942 may be on-demand services that are made available to one or more of the users 984A-S working for one or more other organizations (sometimes referred to as outside users) so that those organizations do not need to necessarily be concerned with building and/or maintaining a system, but instead makes use of the service(s) 942 when needed (e.g., on the demand of the users 984A-S). The service(s) 942 may communication with each other and/or with one or more of the user electronic devices 980A-S via one or more Application Programming Interface(s) (APIs) (e.g., a Representational State Transfer (REST) API). The user electronic devices 980A-S are operated by users 984A-S.

In one implementation, the system 940 is a multi-tenant cloud computing architecture supporting multiple services, such as a customer relationship management (CRM) service (e.g., Sales Cloud by salesforce.com, Inc.), a contracts/proposals/quotes service (e.g., Salesforce CPQ by salesforce.com, Inc.), a customer support service (e.g., Service Cloud and Field Service Lightning by salesforce.com, Inc.), a marketing service (e.g., Marketing Cloud, Salesforce DMP, and Pardot by salesforce.com, Inc.), a commerce service (e.g., Commerce Cloud Digital, Commerce Cloud Order Management, and Commerce Cloud Store by salesforce.com, Inc.), communication with external business data sources (e.g., Salesforce Connect by salesforce.com, Inc.), a productivity service (e.g., Quip by salesforce.com, Inc.), database as a service (e.g., Database.com™ by salesforce.com, Inc.), Data as a Service (DAAS) (e.g., Data.com by salesforce.com, Inc.), Platform as a Service (PAAS) (e.g., execution runtime and application (app) development tools; such as, Heroku™ Enterprise, Thunder, and Force.com® and Lightning by salesforce.com, Inc.), an analytics service (e.g., Einstein Analytics, Sales Analytics, and/or Service Analytics by salesforce.com, Inc.), a community service (e.g., Community Cloud and Chatter by salesforce.com, Inc.), an Internet of Things (IoT) service (e.g., Salesforce IoT and IoT Cloud by salesforce.com, Inc.), industry specific services (e.g., Financial Services Cloud and Health Cloud by salesforce.com, Inc.), and/or Infrastructure as a Service (IAAS) (e.g., virtual machines, servers, and/or storage). For example, system 940 may include an application platform 944 that enables PAAS for creating, managing, and executing one or more applications developed by the provider of the application platform 944, users accessing the system 940 via one or more of user electronic devices 980A-S, or third-party application developers accessing the system 940 via one or more of user electronic devices 980A-S.

In some implementations, one or more of the service(s) 942 may utilize one or more multi-tenant databases 946 for tenant data 948, as well as system data storage 950 for system data 952 accessible to system 940. In certain implementations, the system 940 includes a set of one or more servers that are running on server electronic devices and that are configured to handle requests for any authorized user associated with any tenant (there is no server affinity for a user and/or tenant to a specific server). The user electronic devices 980A-S communicate with the server(s) of system 940 to request and update tenant-level data and system-level data hosted by system 940, and in response the system 940 (e.g., one or more servers in system 940) automatically may generate one or more Structured Query Language (SQL) statements (e.g., one or more SQL queries) that are designed to access the desired information from the one or more multi-tenant database 946 and/or system data storage 950.

In some implementations, the service(s) 942 are implemented using virtual applications dynamically created at run time responsive to queries from the user electronic devices 980A-S and in accordance with metadata, including: 1) metadata that describes constructs (e.g., forms, reports, workflows, user access privileges, business logic) that are common to multiple tenants; and/or 2) metadata that is tenant specific and describes tenant specific constructs (e.g., tables, reports, dashboards, interfaces, etc.) and is stored in a multi-tenant database. To that end, the program code 960 may be a runtime engine that materializes application data from the metadata; that is, there is a clear separation of the compiled runtime engine (also known as the system kernel), tenant data, and the metadata, which makes it possible to independently update the system kernel and tenant-specific applications and schemas, with virtually no risk of one affecting the others. Further, in one implementation, the application platform 944 includes an application setup mechanism that supports application developers' creation and management of applications, which may be saved as metadata by save routines. Invocations to such applications, including the transaction queue 104A, the tenant level objects 104B, the network level objects 104C, and the blockchain services 104D, may be coded using Procedural Language/Structured Object Query Language (PL/SOQL) that provides a programming language style interface. A detailed description of some PL/SOQL language implementations is discussed in U.S. Pat. No. 7,730,478 entitled, METHOD AND SYSTEM FOR ALLOWING ACCESS TO DEVELOPED APPLICATIONS VIA A MULTI-TENANT ON-DEMAND DATABASE SERVICE, by Craig Weissman, filed Sep. 21, 2007. Invocations to applications may be detected by one or more system processes, which manages retrieving application metadata for the tenant making the invocation and executing the metadata as an application in a software container (e.g., a virtual machine).

Network 982 may be any one or any combination of a LAN (local area network), WAN (wide area network), telephone network, wireless network, point-to-point network, star network, token ring network, hub network, or other appropriate configuration. The network may comply with one or more network protocols, including an Institute of Electrical and Electronics Engineers (IEEE) protocol, a 3rd Generation Partnership Project (3GPP) protocol, or similar wired and/or wireless protocols, and may include one or more intermediary devices for routing data between the system 940 and the user electronic devices 980A-S.

Each user electronic device 980A-S (such as a desktop personal computer, workstation, laptop, Personal Digital Assistant (PDA), smart phone, etc.) typically includes one or more user interface devices, such as a keyboard, a mouse, a trackball, a touch pad, a touch screen, a pen or the like, for interacting with a graphical user interface (GUI) provided on a display (e.g., a monitor screen, a liquid crystal display (LCD), etc.) in conjunction with pages, forms, applications and other information provided by system 940. For example, the user interface device can be used to access data and applications hosted by system 940, and to perform searches on stored data, and otherwise allow a user 984 to interact with various GUI pages that may be presented to a user 984. User electronic devices 980A-S might communicate with system 940 using TCP/IP (Transfer Control Protocol and Internet Protocol) and, at a higher network level, use other networking protocols to communicate, such as Hypertext Transfer Protocol (HTTP), FTP, Andrew File System (AFS), Wireless Application Protocol (WAP), File Transfer Protocol (FTP), Network File System (NFS), an application program interface (API) based upon protocols such as Simple Object Access Protocol (SOAP), Representational State Transfer (REST), etc. In an example where HTTP is used, one or more user electronic devices 980A-S might include an HTTP client, commonly referred to as a "browser," for sending and receiving HTTP messages to and from server(s) of system 940, thus allowing users 984 of the user electronic device 980A-S to access, process and view information, pages and applications available to it from system 940 over network 982.

In the above description, numerous specific details such as resource partitioning/sharing/duplication implementations, types and interrelationships of system components, and logic partitioning/integration choices are set forth in order to provide a more thorough understanding. It will be appreciated, however, by one skilled in the art, that the invention may be practiced without such specific details. In other instances, control structures, logic implementations, opcodes, means to specify operands, and full software instruction sequences have not been shown in detail since those of ordinary skill in the art, with the included descriptions, will be able to implement what is described without undue experimentation.

References in the specification to "one implementation," "an implementation," "an example implementation," etc., indicate that the implementation described may include a particular feature, structure, or characteristic, but every implementation may not necessarily include the particular feature, structure, or characteristic. Moreover, such phrases are not necessarily referring to the same implementation. Further, when a particular feature, structure, or characteristic is described in connection with an implementation, it is submitted that it is within the knowledge of one skilled in the art to affect such feature, structure, or characteristic in connection with other implementations whether or not explicitly described.

Bracketed text and blocks with dashed borders (e.g., large dashes, small dashes, dot-dash, and dots) may be used herein to illustrate optional operations and/or structures that add additional features to some implementations. However, such notation should not be taken to mean that these are the only options or optional operations, and/or that blocks with solid borders are not optional in certain implementations.

In the following description and claims, the term "coupled," along with its derivatives, may be used. "Coupled" is used to indicate that two or more elements, which may or may not be in direct physical or electrical contact with each other, co-operate or interact with each other.

The operations in the flow diagrams are be described with reference to the exemplary implementations in the other figures. However, the operations of the flow diagrams can be performed by implementations other than those discussed with reference to the other figures, and the implementations discussed with reference to these other figures can perform operations different than those discussed with reference to the flow diagrams.

While the flow diagrams in the figures show a particular order of operations performed by certain implementations, it should be understood that such order is exemplary (e.g., alternative implementations may perform the operations in a different order, combine certain operations, overlap certain operations, etc.).

While the above description includes several exemplary implementations, those skilled in the art will recognize that the invention is not limited to the implementations described and can be practiced with modification and alteration within the spirit and scope of the appended claims. The description is thus illustrative instead of limiting.

What is claimed is:

1. A method for a multi-tenant server to manage data in a peer-to-peer blockchain network, the method comprising:
    monitoring, by the multi-tenant server, one or more fields of a first physical object of a first tenant in the peer-to-peer blockchain network to determine when one or more conditions of a smart contract have been fulfilled;
    determining, by the multi-tenant server, that one or more conditions of the smart contract have been met by the first physical object of the first tenant;
    performing, by the multi-tenant server, one or more operations of the smart contract, which are associated with the one or more conditions, in response to determining that the one or more conditions of the smart contract have been met by the first physical object of the first tenant,
    wherein the one or more operations are performed in relation to a second physical object of a second tenant in the peer-to-peer blockchain network; and
    generating, by the multi-tenant server, an exchange object for the peer-to-peer blockchain network, wherein the exchange object includes a set of exchange fields and a mapping between each exchange field in the set of exchange fields and fields of the first physical object, the second physical object, and a third physical object, which corresponds to a third tenant in the peer-to-peer blockchain network.

2. The method of claim 1, wherein the one or more operations include:
    generating, by the multi-tenant server on behalf of the second tenant in the peer-to-peer blockchain network, a transaction object; and
    making, by the multi-tenant server on behalf of the second tenant, the transaction object available to the third tenant in the peer-to-peer blockchain network to attempt to obtain consensus for altering the third physical object corresponding to the third tenant based on data in the second physical object of the second tenant.

3. The method of claim 2, wherein the transaction object includes the set of exchange fields and data values from the second physical object in exchange fields corresponding to the mapping.

4. The method of claim 2, further comprising:
    determining, by the multi-tenant server, a consensus for adding the smart contract to the peer-to-peer blockchain network.

5. The method of claim 4, further comprising:
    committing, by the multi-tenant server, the smart contract to the peer-to-peer blockchain network in response to determining consensus for the smart contract in the peer-to-peer blockchain network,
    wherein committing the smart contract to the peer-to-peer blockchain network includes adding a first set of blocks to ledgers of all tenants in the peer-to-peer blockchain network, including the first tenant, the second tenant, and the third tenant.

6. The method of claim 5, further comprising:
    determining, by the multi-tenant server, a consensus for a modification to the smart contract in the peer-to-peer blockchain network; and
    committing, by the multi-tenant server, the modification to the smart contract to the peer-to-peer blockchain network in response to determining consensus for the modification in the peer-to-peer blockchain network,
    wherein committing the modification to the peer-to-peer blockchain network includes adding a second set of blocks to the ledgers of all the tenants in the peer-to-peer blockchain network, including the first tenant, the second tenant, and the third tenant.

7. A non-transitory machine-readable storage medium, including instructions that when executed by a processor of a multi-tenant server, cause the processor to:
    monitor one or more fields of a first physical object of a first tenant in the peer-to-peer blockchain network to determine when one or more conditions of a smart contract have been fulfilled;
    determine that one or more conditions of the smart contract have been met by the first physical object of the first tenant;
    perform one or more operations of the smart contract, which are associated with the one or more conditions, in response to determining that the one or more conditions of the smart contract have been met by the first physical object of the first tenant,
    wherein the one or more operations are performed in relation to a second physical object of a second tenant in the peer-to-peer blockchain network; and
    generate, by the multi-tenant server, an exchange object for the peer-to-peer blockchain network, wherein the exchange object includes a set of exchange fields and a mapping between each exchange field in the set of exchange fields and fields of the first physical object, the second physical object, and a third physical object, which corresponds to a third tenant in the peer-to-peer blockchain network.

8. The non-transitory machine-readable storage medium of claim 7, wherein the one or more operations include:
generating, by the multi-tenant server on behalf of the second tenant in the peer-to-peer blockchain network, a transaction object; and
making, by the multi-tenant server on behalf of the second tenant, the transaction object available to the third tenant in the peer-to-peer blockchain network to attempt to obtain consensus for altering the third physical object corresponding to the third tenant based on data in the second physical object of the second tenant.

9. The non-transitory machine-readable storage medium of claim 8, wherein the transaction object includes the set of exchange fields and data values from the second physical object in exchange fields corresponding to the mapping.

10. The non-transitory machine-readable storage medium of claim 8, wherein the instructions further cause the processor to:
determine a consensus for adding the smart contract to the peer-to-peer blockchain network.

11. The non-transitory machine-readable storage medium of claim 10, wherein the instructions further cause the processor to:
commit the smart contract to the peer-to-peer blockchain network in response to determining consensus for the smart contract in the peer-to-peer blockchain network,
wherein committing the smart contract to the peer-to-peer blockchain network includes adding a first set of blocks to ledgers of all tenants in the peer-to-peer blockchain network, including the first tenant, the second tenant, and the third tenant.

12. The non-transitory machine-readable storage medium of claim 11, wherein the instructions further cause the processor to:
determine a consensus for a modification to the smart contract in the peer-to-peer blockchain network; and
commit the modification to the smart contract to the peer-to-peer blockchain network in response to determining consensus for the modification in the peer-to-peer blockchain network,
wherein committing the modification to the peer-to-peer blockchain network includes adding a second set of blocks to the ledgers of all the tenants in the peer-to-peer blockchain network, including the first tenant, the second tenant, and the third tenant.

13. A multi-tenant server to manage data in a peer-to-peer blockchain network, the multi-tenant server comprising:
a processor;
a memory storing instruction that when executed by the processor cause the processor to:
monitor one or more fields of a first physical object of a first tenant in the peer-to-peer blockchain network to determine when one or more conditions of a smart contract have been fulfilled;
determine that one or more conditions of the smart contract have been met by the first physical object of the first tenant;
perform one or more operations of the smart contract, which are associated with the one or more conditions, in response to determining that the one or more conditions of the smart contract have been met by the first physical object of the first tenant,
wherein the one or more operations are performed in relation to a second physical object of a second tenant in the peer-to-peer blockchain network; and
generate, by the multi-tenant server, an exchange object for the peer-to-peer blockchain network, wherein the exchange object includes a set of exchange fields and a mapping between each exchange field in the set of exchange fields and fields of the first physical object, the second physical object, and a third physical object, which corresponds to a third tenant in the peer-to-peer blockchain network.

14. The multi-tenant server of claim 13, wherein the one or more operations include:
generating, by the multi-tenant server on behalf of the second tenant in the peer-to-peer blockchain network, a transaction object; and
making, by the multi-tenant server on behalf of the second tenant, the transaction object available to the third tenant in the peer-to-peer blockchain network to attempt to obtain consensus for altering the third physical object corresponding to the third tenant based on data in the second physical object of the second tenant.

15. The multi-tenant server of claim 14, wherein the transaction object includes the set of exchange fields and data values from the second physical object in exchange fields corresponding to the mapping.

16. The multi-tenant server of claim 14, wherein the instructions further cause the processor to:
determine a consensus for adding the smart contract to the peer-to-peer blockchain network.

17. The multi-tenant server of claim 16, wherein the instructions further cause the processor to:
commit the smart contract to the peer-to-peer blockchain network in response to determining consensus for the smart contract in the peer-to-peer blockchain network,
wherein committing the smart contract to the peer-to-peer blockchain network includes adding a first set of blocks to ledgers of all tenants in the peer-to-peer blockchain network, including the first tenant, the second tenant, and the third tenant.

* * * * *